(12) United States Patent
Mohajeri et al.

(10) Patent No.: US 11,197,931 B2
(45) Date of Patent: Dec. 14, 2021

(54) LIQUID INJECTABLE COPOLYMER

(71) Applicant: Queen's University at Kingston, Kingston (CA)

(72) Inventors: Sara Mohajeri, Milton (CA); Brian G. Amsden, Kingston (CA); Fei Chen, Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 16/182,843

(22) Filed: Nov. 7, 2018

(65) Prior Publication Data

US 2019/0134202 A1 May 9, 2019

Related U.S. Application Data

(60) Provisional application No. 62/582,511, filed on Nov. 7, 2017.

(51) Int. Cl.

| | |
|---|---|
| *A61K 47/34* | (2017.01) |
| *A61K 31/573* | (2006.01) |
| *A61L 31/16* | (2006.01) |
| *A61L 31/14* | (2006.01) |
| *A61L 31/10* | (2006.01) |
| *A61L 31/06* | (2006.01) |
| *A61K 9/00* | (2006.01) |
| *C08G 64/16* | (2006.01) |
| *A61L 29/14* | (2006.01) |
| *A61L 29/16* | (2006.01) |
| *A61L 29/08* | (2006.01) |
| *A61L 27/58* | (2006.01) |
| *A61K 9/08* | (2006.01) |
| *A61L 27/54* | (2006.01) |
| *C08G 64/30* | (2006.01) |
| *A61L 27/34* | (2006.01) |

(52) U.S. Cl.
CPC ............ *A61K 47/34* (2013.01); *A61K 9/0014* (2013.01); *A61K 9/0019* (2013.01); *A61K 9/0024* (2013.01); *A61K 9/0029* (2013.01); *A61K 9/08* (2013.01); *A61K 31/573* (2013.01); *A61L 27/34* (2013.01); *A61L 27/54* (2013.01); *A61L 27/58* (2013.01); *A61L 29/085* (2013.01); *A61L 29/148* (2013.01); *A61L 29/16* (2013.01); *A61L 31/06* (2013.01); *A61L 31/10* (2013.01); *A61L 31/148* (2013.01); *A61L 31/16* (2013.01); *C08G 64/1608* (2013.01); *C08G 64/305* (2013.01); *A61L 2300/252* (2013.01); *A61L 2300/256* (2013.01); *A61L 2300/258* (2013.01); *A61L 2300/416* (2013.01); *A61L 2300/43* (2013.01); *A61L 2300/606* (2013.01); *A61L 2400/06* (2013.01); *A61L 2420/00* (2013.01)

(58) Field of Classification Search
CPC .... A61K 47/34; A61K 31/573; A61K 9/0029; A61K 9/0019; A61K 9/0014; A61K 9/08; A61K 9/0024; A61L 31/16; A61L 31/148; A61L 31/10; A61L 31/06; A61L 29/148; A61L 29/16; A61L 29/085; A61L 27/58; A61L 27/54; A61L 27/34; A61L 2300/43; A61L 2400/06; A61L 2420/00; A61L 2300/606; A61L 2300/258; A61L 2300/416; A61L 2300/252; A61L 2300/256; C08G 64/1608; C08G 64/305
See application file for complete search history.

(56) References Cited

U.S. PATENT DOCUMENTS

| | | |
|---|---|---|
| 5,442,033 A | 8/1995 | Bezwada |
| 5,631,015 A | 5/1997 | Bezwada et al. |
| 7,005,136 B2 | 2/2006 | Nathan et al. |
| 2007/0280988 A1* | 12/2007 | Ludwig .................. A61L 27/34 424/423 |

OTHER PUBLICATIONS

Xu-Li Wang, et al, Synthesis, Characterization and In Vitro Cytotoxicity of Poly[(5-benxyloxy-trimethylene carbonate)-co-(trimethylene carbonate)], 203 Macromol. Chem. Phys. 985 (Year: 2002).*
Xiaolin Zhang, et al, Amphiphilic Triblock Copolycarbonates with Poly(Glycerol carbonate) as Hydrophilic Blocks, 42 Macromol. 1010 (Year: 2009).*
Jesse B. Wollinsky, et al, Poly(carbonate ester)s Based on Units of 6-Hydroxyhexanoic Acid and Glycerol, 40 Macromol. 7065 (Year: 2007).*
Laurianne Timbart, et al, Low Viscosity Poly(trimethylene carbonate) for Localized Drug Delivery: Rheological Properties and in vivo Degradation, 9 Macromol. Biosci. 786 (Year: 2009).*
Jiajie Hua, et al, Influence of Chain Microstructure on the Hydrolytic Degradation of Copolymers from 1,3-Trimethylene Carbonate and L-Lactide, 47 J Pol. Sci Part A: Poly. Chem. 3869 (Year: 2009).*

(Continued)

*Primary Examiner* — Sean M Basquill
(74) *Attorney, Agent, or Firm* — Stephen J. Scribner

(57) ABSTRACT

The invention provides liquid injectable copolymers of TMC and HTMC that are degradable in vivo. Degradation can be tailored by adjusting the amount of HTMC in the copolymer, the initial molecular weight of the copolymer, and the characteristics of the initiator used in its preparation. Specifically, the degradation rate increases as the amount of HTMC incorporated into the copolymer increases, as the molecular weight of the copolymer decreases, and as the hydrophobicity of the initiator decreases. Moreover, the degradation yields products such as glycerol and carbon dioxide that are non-toxic in vivo, and which will not cause a substantive change in tissue pH upon implantation in vivo. The copolymers may be used in applications such as drug delivery and as coatings.

29 Claims, 16 Drawing Sheets

(56) References Cited

OTHER PUBLICATIONS

Hatefi, A. et al., "Biodegradable injectable in situ forming drug delivery systems", J. of Controlled Release, vol. 80, pp. 9-28 (2002).
Amsden, B.G., "Liquid, Injectable, Hydrophobic and Biodegradable Polymers as Drug Delivery Vehicles", Macromol. Biosci. vol. 10, pp. 825-835 (2010).
Van de Weert, M. et al., "Reversible aggregation of lysozyme in a biodegradable amphiphilic multiblock copolymer", Eur. J. of Pharm. Biopharm., vol. 54, pp. 89-93 (2002).
Schwach-Abdellaoui, K. et al,. "Bioerodible injectable poly(ortho ester) for Tetracycline Controlled Delivery to Periodontal Pockets: Preliminary Trial in Humans", AAPS Pharmsci. Vol. 4, Article 20, pp. 1-7, (2002).
Schwach-Abdellaoui, K. et al,. "Control of Molecular Weight for Auto-Catalyzed Poly(ortho ester) Obtained by Polycondensation Reaction", International Journal of Polymer Analysis and Characterization, vol. 7, pp. 145-161, (2002).
Hatefi, A. et al., "A Biodegradable Injectable Thermoplastic for Localized Camptothecin Delivery", J. Pharm. Sci. vol. 93, pp. 1195-1204, (2004).
Sokolsky-Papkov, M. et al., Prolonged Local Anesthetic Action Through Slow Release from Poly (Lactic Acid Co Castor Oil). Pharm Res. vol. 26, pp. 32-39, (2009).
Trimaille, T., et al., "Poly(hexyl-substituted lactides): Novel injectable hydrophobic drug delivery systems", J. Biomed. Mater. Res., Part A. 80A, pp. 55-65, (2007).
Bundgaard, H. et al., "Pro-Drugs as Drug Delivery Systems XVII. Esters of 4-Hydroxybutyric Acids as Potential Pro-Drug Types for Gamma-Lactones", Int. J. Pharm. vol. 7, pp. 169-176, (1980).
De Gracia Lux, C., et al., Intramolecular Cyclization Assistance for Fast Degradation of Ornithine-Based Poly (ester amide)s, J Polym Sci Part A-1: Polym Chem. 51, pp. 3783-3790, (2013).
Timbart, L., et al., Low Viscosity Poly(trimethylene carbonate) for Localized Drug Delivery: Rheological Properties and in vivo Degradation, Macromol. Biosci., vol. 9, pp. 786-794, (2009).
Babasola, I.O., et al., Surface Eroding, Liquid injectable Polymers Based on 5-Ethylene Ketal ε-Caprolactone, Biomacromolecules, vol. 12, pp. 3423-3431, (2011).
Babasola, I.O., et al., "Osmotic pressure driven protein release from viscous liquid, hydrophobic polymers based on 5-ethylene ketal ε-caprolactons: Potential and mechanism", Eur. J. Pharm. Biopharm., vol. 85, pp. 765-772, (2013).
Jain, J.P., et al., "Hydroxy fatty acid based polyanhydride as drug delivery system: Synthesis, characterization, in vitro degradation, drug release, and biocompatibiity", J. Biomed. Mater. Res., Part A. 84A, pp. 740-752, (2008).
Amsden, B. et al., "Development of Biodegradable Injectable Thermoplastic Oligomers", Biomacromolecules, vol. 5, pp. 637-642, (2004).
Yu, F., et al., "Synthesis and Characterization of OH-Terminated Poly(trimethylene carbonate)s by Alcohol-Initiated Ring-Opening Polymerization in Melt Bulk without Using Any Catalyst", Polymer Journal, vol. 36, No. 1, pp. 28-33, (2004).
Molea, G., et al., Comparative study on biocompatibility and absorption times of three absorbable monofilament suture materials (Polydioxanone, Poliglecaprone 25, Glycomer 631), Br. J. Plast. Surg., vol. 53, pp. 137-141, (2000).
Asmus, L.R., et al., "Solutions as solutions—Synthesis and use of a liquid polyester excipient to dissolve lipophilic drugs and formulate sustained-release parenterals", Eur. J. Pharm. Biopharm., vol. 79, pp. 584-591, (2011).
Asmus, L.R., et al., "Injectable formulations for an intravitreal sustained-release application of a novel single-chain VEGF antibody fragment", Eur. J. Pharm. Biopharm., vol. 95, pp. 250-260, (2015).
Bundgaard, H. et al., Pilocarpine Prodrugs I. Synthesis, Physicochemical Properties and Kinetics of Lactonization of Pilocarpic Acid Esters, J. Pharm. Sci., vol. 75, pp. 36-43, (1986).
Asmus, L.R., et al., "In vivo biocompatibility, sustained-release and stability of triptorelin formulations based on a liquid, degradable polymer", J. Controlled Release, vol. 165, pp. 199-206, (2013).
Wang, X-L., et al., "Synthesis and Characterization of Novel Aliphatic Polycarbonates", J. Polym. Sci. Part A-1: Polym. Chem., vol. 40, pp. 70-75, (2002).
Wang, X-L., et al., Synthesis, Characterization and In Vitro Cytotoxicity of Poly[(5-benzloxy-trimethylene carbonate)-co-(trimethylene carbonate)], Macromol. Chem. Physic. vol. 203, pp. 985-990, (2002).
Ray, W.C. et al., "Polycarbonate and Poly(carbonate-ester)s Synthesized from Biocompatible Building Blocks of Glycerol and Lactic Acid", Macromolecules, vol. 36, pp. 3557-3562, (2003).
Zhang, H. et al., "Synthesis of Atactic and Isotactic Poly(1,2-glycerol carbonate)s: Degradable Polymers for Biomedical and Pharmaceutical Applications", J. Am. Chem. Soc., vol. 135, pp. 6806-6809, (2013).
Wolinsky, J.B. et al., "Functionalized Hydrophobic Poly(glycerol-co-ε-caprolactone) Depots for Controlled Drug Release", Biomacromolecules, vol. 13, pp. 406-411, (2012).
Cheng, S-X., et al., "Synthesis and Characterization of Novel Biodegradable Copolymers of 5-Benzloxy-1,3-dioxan-2-one and Glycolide", Maoromo.l Rapid Comm., vol. 24, pp. 1066-1069, (2003).
Zhang, X., et al. "Amphiphilic Triblock Copolycarbonates with Poly(glycerol carbonate) as Hydrophilic Blocks", Macromolecules, vol. 42, pp. 1010-1016, (2009).
Lai, K-L., et al., "Synthesis of Functionalizable and Biodegradable Polymers via Ring-Opening Polymerization of 5-Benzyloxy-Trimethylene Carbonate and ε-Caprolactone", J. Appl. Polym. Sci., vol. 123, pp. 2204-2210, (2011).
Storey, R.F., et al., "Kinetics and Mechanism of the Stannous Octaate-Catalyzed Bulk Polymerization of ε-Caprolactone", Marcomolecules, vol. 35, pp. 1504-1512, (2002).

* cited by examiner

LIQUID INJECTABLE COPOLYMER

RELATED APPLICATION

This application claims the benefit of the filing date of Application No. 62/582,511, filed on Nov. 7, 2017, the contents of which are incorporated herein by reference in their entirety.

BACKGROUND

There is a clinical need for localized drug administration providing sustained and/or controlled release for the treatment of numerous conditions, including ischemia, chronic pain, diabetes, and cancer. Reasons for requiring such delivery include minimizing patient exposure to the drug thus decreasing systemic toxicity, improving therapeutic results by achieving effective concentrations of the drug in the desired site for sufficient time frames, and minimizing the overall amount of drug to be administered. To meet this need, polymer formulations have been investigated that can be injected directly into the required site without the need for surgical implantation and retrieval. Such formulations include in situ forming hydrogels and organogels, biodegradable polymer microspheres and nanoparticles, in situ precipitating polymer solutions, and viscous liquid, biodegradable polymers possessing melting points below body temperature.

A formulation based on viscous liquid, hydrophobic, biodegradable polymers provides for facile incorporation of thermally sensitive drugs such as proteins and peptides by simple mixing, as well as injectability through standard gauge needles. In addition, the liquid nature of the polymer may limit local mechanical irritation to the surrounding tissue. Moreover, in some formulations the viscosity and thus the injectability of the polymers can be controlled.[2]

A number of viscous liquid polymer compositions have been examined as injectable depots for drug delivery, including: poly(ortho esters) [3-5], low molecular weight poly($\alpha$-hydroxy acids) [1, 6-9], hexyl-substituted poly(lactide) [10], poly(trimethylene carbonate) [11], branched, ester linked, fatty acid polymers from the reaction of glyceryl monolinoleate with succinic anhydride [12], copolymers of $\epsilon$-ethylene ketal $\epsilon$-caprolactone and D,L-lactide [13, 14], and low molecular weight fatty-acid based polyanhydrides [15]. While all these polymers provide injectability and depot formation, with the exception of poly(trimethylene carbonate) they degrade to form acidic degradation products. The accumulation of these acidic degradation products within the depot may cause degradation of acid-sensitive drugs. This issue is particularly relevant to the delivery of peptides and protein drugs. Moreover, the accumulation of these acidic degradation products in the tissue has been implicated in local tissue irritation. Poly(trimethylene carbonate) does not produce acidic products upon its in vivo degradation as it does not undergo hydrolysis, but rather is degraded through enzymatic action and the production of reactive oxygen species by activated macrophages at the polymer interface. Additionally, the in vivo degradation rate of some of these polymers is not controllable.

SUMMARY

According to one aspect of the invention there is provided a liquid, injectable, degradable copolymer comprising trimethylene carbonate (TMC), 5-hydroxy trimethylene carbonate (HTMC), and an initiator. As described herein, embodiments of the liquid, injectable, degradable copolymer degrade to non-acidic degradation products, and have a controllable degradation rate. The degradation rate may be controlled by adjusting the ratio of TMC:HTMC along with the molecular weight and the hydrophobicity of the copolymer. The hydrophobicity may be controlled by selecting an initiator with a greater or lower hydrophilicity. The invention is based, at least in part, on the discovery that HTMC degrades rapidly at neutral pH, even for polymers with very high molecular weights (e.g., ~40 kDa degraded within hours). The degradation rate may be adjusted by copolymerizing HTMC with TMC, which does not undergo degradation at these conditions and does not form acidic products.

In various embodiments, degradation rate of the copolymer may be controlled according to at least one of a monomer composition, an initiator, and a molecular weight (MW) of the copolymer, and the copolymer remains as a viscous liquid depot, and gradually degrades according to the controlled degradation rate.

In one embodiment, the degradation rate of the copolymer is controlled according to a ratio of TMC:HTMC. The ratio of TMC:HTMC may be from 15:1 to 1:9.

In one embodiment, the viscosity of the copolymer is related to an amount of the initiator, wherein the amount of the initiator is selected to be from about 1% w/w to about 50% w/w of the MW of the copolymer, or from about 10% w/w to about 50% w/w of the MW of the copolymer, or from about 25% w/w to about 50% w/w of the MW of the copolymer. The initiator may comprise an alcohol.

In various embodiments, the initiator comprises at least one of an alcohol, an amine, a thiol, and a carboxylic acid.

In various embodiments, the MW of the copolymer is from about 500 Da to about 5000 Da.

In various embodiments, the copolymer is biodegradable in vivo; wherein degradation yields products that are non-irritating and/or non-toxic and do not cause a substantive change in tissue pH in vivo.

Embodiments may comprise at least one drug. The drug may comprise a therapeutic compound, pharmaceutical, biopharmaceutical, bioactive agent, medicament, antineoplastic, hormone, peptide, protein, nucleic acid, vector, virus, antigen, antibody, or combination thereof. Embodiments may be used as a drug delivery vehicle, and/or as a coating on a surgical device or instrument, or for use as a coating on a surgical device or instrument for drug release. Embodiments may be used as a cohesive drug delivery depot.

Another aspect of the invention provides a method for preparing an injectable, degradable, liquid copolymer, comprising: combining a copolymer of trimethylene carbonate (TMC) and 5-hydroxy trimethylene carbonate (HTMC) together with an initiator, and selecting at least one of a monomer composition, an initiator, and a molecular weight (MW) of the copolymer to control a degradation rate of the copolymer; wherein the copolymer remains as a viscous liquid depot, and gradually degrades according to the controlled degradation rate.

The method may comprise selecting an amount of the initiator to be from about 1% w/w to about 50% w/w of the MW of the copolymer, or from about 10% w/w to about 50% w/w of the MW of the copolymer, or from about 25% w/w to about 50% w/w of the MW of the copolymer, wherein a viscosity of the copolymer is related to the amount of the initiator.

The method may comprise selecting a ratio of TMC:HTMC to control a degradation rate of the copolymer.

The method may comprise selecting the MW of the copolymer to be from about 500 Da to about 5000 Da.

The method may comprise combining at least one drug with the copolymer. The drug may be at least one drug selected from a therapeutic compound, pharmaceutical, biopharmaceutical, bioactive agent, medicament, antineoplastic, hormone, peptide, protein, nucleic acid, vector, virus, antigen, antibody, or combination thereof.

Another aspect of the invention provides a method for delivering at least one drug, comprising: combining the at least one drug with the injectable, degradable, liquid copolymer as described herein, such that a cohesive drug delivery depot is prepared; and administering the cohesive drug delivery depot to a subject. The drug may comprise a therapeutic compound, pharmaceutical, biopharmaceutical, bioactive agent, medicament, antineoplastic, hormone, peptide, protein, nucleic acid, vector, virus, antigen, antibody, or combination thereof. The cohesive drug delivery depot may be administered by a route selected from parenteral, topical, and transdermal.

BRIEF DESCRIPTION OF THE DRAWINGS

To better understand the invention, and to show more clearly how it may be carried into effect, embodiments will be described, by way of example, with reference to the accompanying drawings, wherein.

DETAILED DESCRIPTION OF EMBODIMENTS

Figure 1:
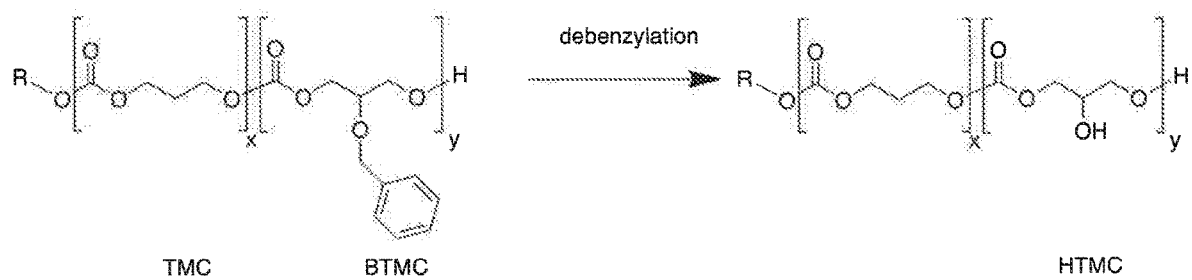
FIG. 1 is a diagram showing a copolymer chemical structure, wherein x and y refer to the number of repeating units of TMC and BTMC or HTMC along the copolymer backbone, and R refers to an initiator, according to an embodiment.

Embodiments described herein address the shortcomings of prior compositions by providing a viscous liquid degradable copolymer that can be readily injected or implanted into a subject to form a cohesive drug delivery depot in vivo, and which does not form acidic degradation products. As described herein, a delivery vehicle containing one or more proteins achieves a locally sustained release of a controlled dose of the one or more proteins while preserving protein bioactivity. According to the embodiments, delivery vehicles are biocompatible and may be implanted via a minimally invasive technique while providing stable healing without significant ongoing inflammation or irritation.

As used herein, the term "cohesive" refers to a single geometrical form, in that the liquid copolymer does not disperse into many droplets but remains substantially as a single unit or, e.g., two or three units, when injected. This is advantageous as it provides for predictable release profiles for drugs.

As used herein, the terms "without significant ongoing inflammation or irritation" and "non-irritating" mean that delivery vehicles and depots according to the embodiments do not cause significant inflammation or other discomfort in a part of a subject's body where they are implanted, and do not stimulate an organism, cell, or organ to produce an active response.

According to the embodiments, there is minimal or substantially no curing of the liquid copolymer when injected, such that it remains as a viscous liquid depot, and gradually degrades according to a controlled degradation rate. In some embodiments, the release rate of a drug may be affected by the degradation rate of the copolymer, such that the drug release rate may be controlled by the degradation rate. In other embodiments the release rate of a drug may be minimally or substantially unaffected by the degradation rate of the copolymer, such that the release rate is substantially independent of the degradation rate.

Embodiments include low molecular weight copolymers of trimethylene carbonate (TMC) and 5-hydroxy trimethylene carbonate (HTMC), together with an initiator. In some embodiments, the degradation rate may be controlled by selecting a ratio of TMC:HTMC, such as, for example, 15:1 to 1:9, wherein the degradation rate increases as the amount of HTMC increases. In other embodiments, the degradation rate may be controlled by selecting a molecular weight (MW) range of the copolymer. In further embodiments, the degradation rate may be controlled by selecting a ratio of TMC:HTMC and according to the amount of initiator included in the copolymer. In some embodiments the MW of the copolymer may be controlled according to the amount of initiator included in the polymer. Unlike prior approaches (e.g., [2, 16]) the initiator remains in the copolymer and may make up a significant portion of the MW of the polymer, such as, for example, 10-50%, or 25-50%. The more hydrophilic the initiator, the faster the degradation of the copolymer. The more flexible the initiator the lower the viscosity of the copolymer. Selecting the amount of initiator as such may be used to adjust the degradation rate and viscosity of the copolymer. Blends of two or more such copolymers may be prepared to tailor properties for specific applications.

As used herein, the term "drug" is intended to refer to any therapeutic compound, pharmaceutical, biopharmaceutical, or bioactive agent, which may include, but is not limited to, for example, a medicament, an antineoplastic, a hormone, peptide or protein, nucleic acid, vector, virus, antigen, or antibody, or any combination of these, dissolved, incorporated or entrapped in a copolymer as described herein and released therefrom. In some embodiments, the drug may be released as the copolymer degrades. In some embodiments, release of the drug may be enhanced or accelerated by degradation of the copolymer. In some embodiments, release of the drug is substantially independent of the degradation of the copolymer.

A copolymer as described herein may be used in applications such as, but not limited to, medicine, veterinary science, immunology, transgenics, management of allergies, treatment of cancer, birth control, tissue engineering, regenerative medicine, as well as other applications where chronic or long-term delivery of a drug is required.

One of ordinary skill in the art, once having the benefit of the disclosure herein, will be able to ascertain particular properties of a liquid copolymer required for a particular purpose, and readily prepare a liquid copolymer that provides such properties.

The cohesive drug delivery depot may be administered in any suitable dosage form such as parenteral, bioerodible ointment, gel, cream, and similar soft dosage forms adapted for the parenteral or topical administration of the drug. Other modes of administration (e.g., transdermal) and compositional forms (e.g., more rigid transdermal forms) are within the scope of the invention as well.

Parenteral formulations of the copolymer may be formulated by mixing one or more drugs with a liquid copolymer. Other suitable parenteral additives may be formulated with the copolymer and drug. However, if water is to be used it should be added immediately before administration. A bioerodible ointment, gel, or cream may also be injected as is or in combination with one or more suitable auxiliary components as described below. Parenteral delivery is preferred for administration of proteinaceous drugs such as growth factors, growth hormone, and the like.

Bioerodible ointments, gels, and creams may include an ointment, gel, or cream base comprising one or more of the copolymers described herein and a selected drug. The drug, whether present as a liquid, a finely divided solid, or any other physical form, is dispersed in the ointment, gel, or cream base. Typically, but optionally, the compositions include one or more other components, e.g., nontoxic auxiliary substances such as colorants, diluents, odorants, carriers, excipients, stabilizers, and the like.

The quantity and type of copolymers incorporated into the parenteral, ointment, gel, cream, etc., are variable. A product may contain blends of the liquid copolymers to provide the desired release profile or consistency to a given formulation.

The amount of drug will be dependent upon the particular drug employed and medical condition being treated. Typically, the amount of drug represents about 0.001% to about 70%, more typically about 0.001% to about 50%, most typically about 0.001% to about 20% by weight of the cohesive drug delivery depot.

A liquid copolymer cohesive drug delivery depot as described herein can be administered with a syringe and needle or a variety of devices. Embodiments may be provided in the form of a kit comprising a device containing the cohesive drug delivery depot. For example, the device may have an outlet, an actuator, and a hollow tubular member fitted to the outlet for administering the cohesive drug delivery depot to a subject.

In another embodiment, a liquid copolymer as described herein may be used to coat a surface of a surgical device or instrument to enhance the lubricity of the coated surface. The liquid copolymer may be applied as a coating using conventional techniques. Examples of the surgical device or instrument include, but are not limited to, sutures, needles, orthopedic pins, clamps, screws, plates, clips, e.g., for vena cava, staples, hooks, buttons, snaps, bone substitutes, e.g., as mandible prosthesis, intrauterine devices, e.g., as spermicidal devices, draining or testing tubes or capillaries, surgical instruments, vascular implants or supports, e.g., stents or grafts, or combinations thereof, vertebral discs, extracorporeal tubing for kidney and heart-lung machines, artificial skin, and supports for cells in tissue engineering applications, all of which may be coated with a liquid copolymer as described herein to improve the surface properties of the device or instrument, and/or to enable the controlled release of a drug from the surface.

Preliminary investigations were conducted using both a low molecular weight hydrophobic drug and a protein drug analog (lysozyme). Copolymers were prepared through the co-polymerization of 5-benzyloxy trimethylene carbonate (BTMC) with TMC via ring-opening polymerization using various catalysts and an initiator to control the molecular weight. As noted above, by selecting the nature (e.g., hydrophobicity) and amount of initiator, the degradation rate and viscosity of the copolymer may be adjusted. Following copolymerization, the BTMC repeating units were debenzylated to yield HTMC repeating units along the backbone. FIG. 1 shows the copolymer chemical structure according to one embodiment, wherein x and y refer to the number of repeating units of TMC and BTMC or HTMC along the copolymer backbone, and R refers to the initiator.

Figure 2A:
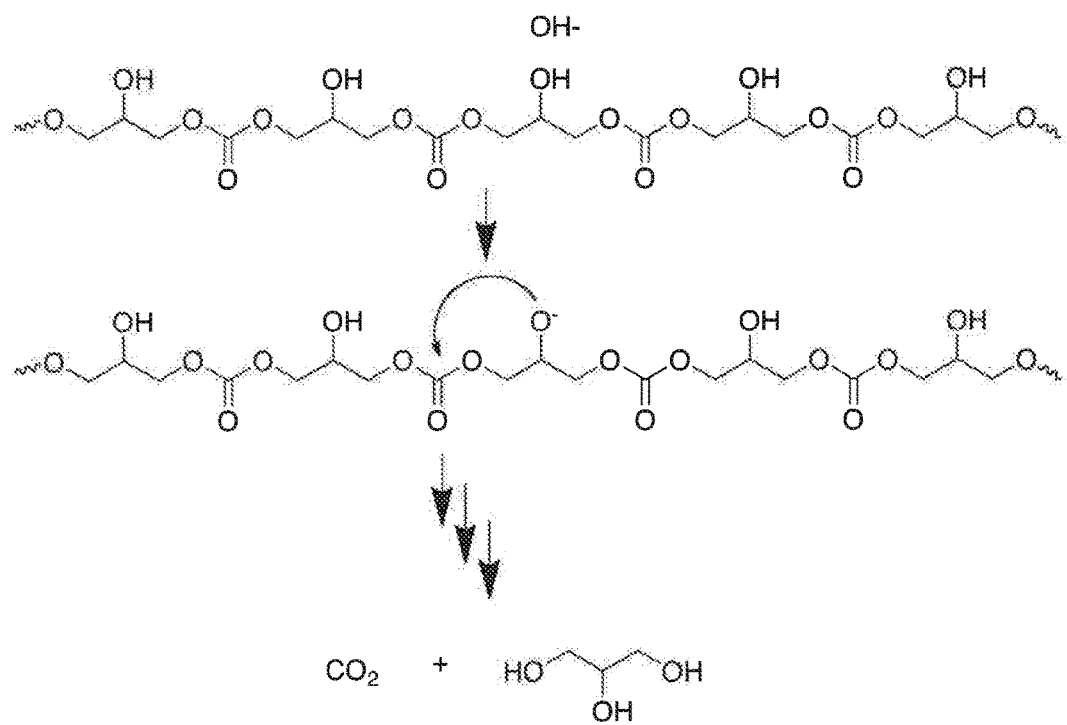
FIGS. 2A and 2B are diagrams showing mechanisms of PHTMC hydrolysis in an alkaline (pH>7) environment.
Figure 2B:
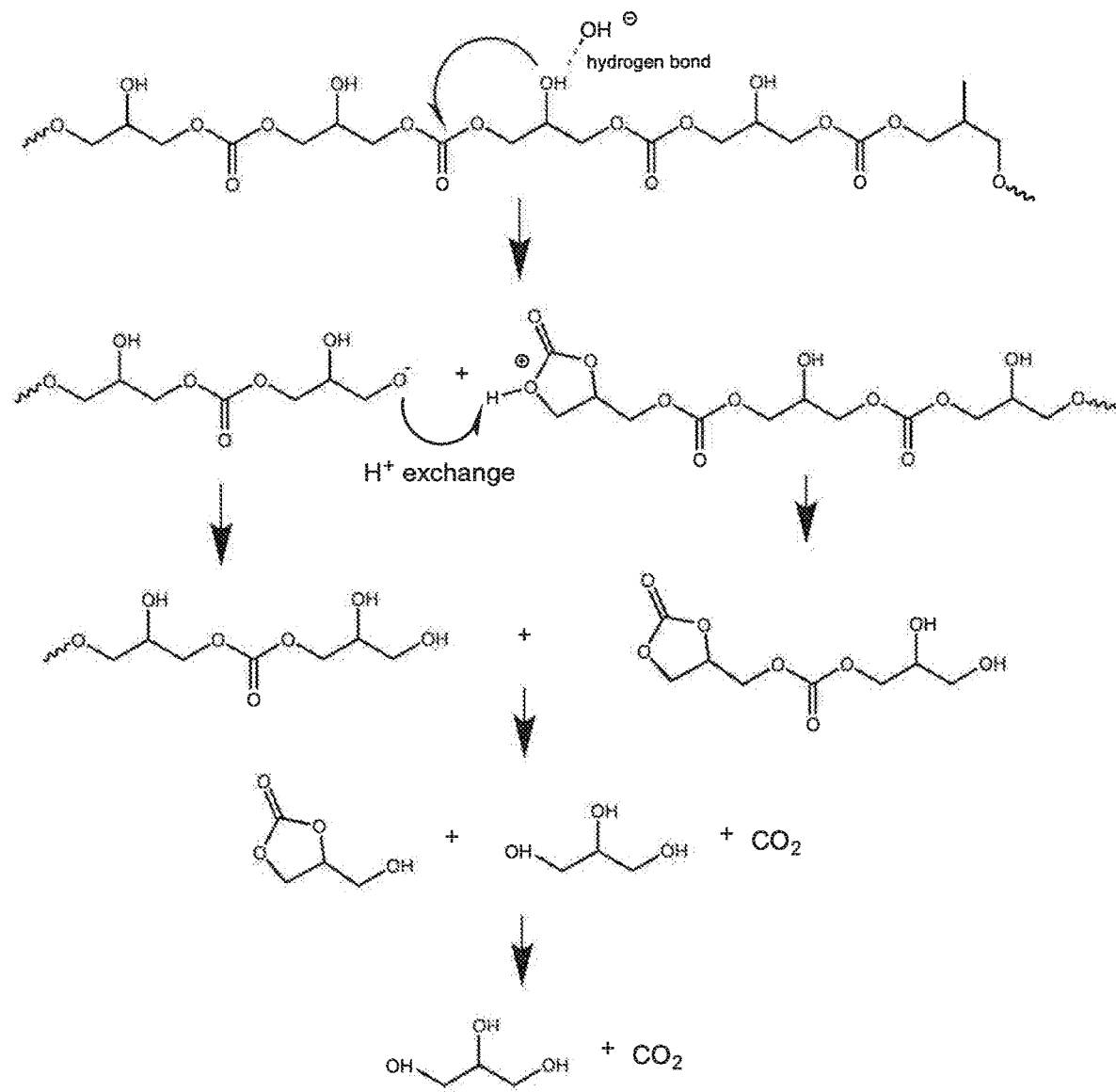
Figure 3:
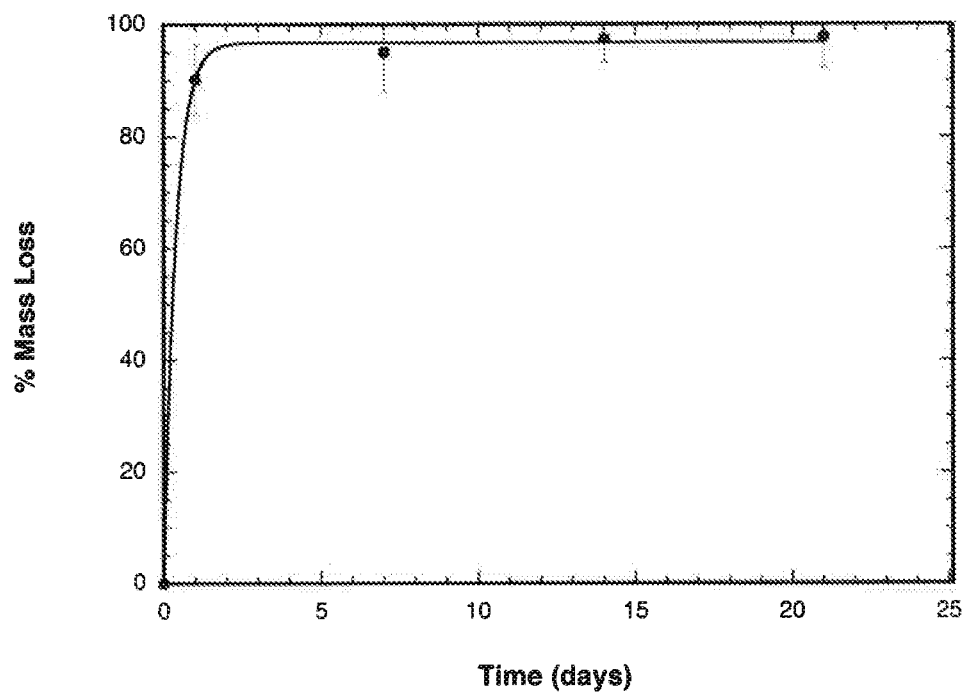
FIG. 3 is a plot showing mass loss with time of 12,750 Da PHTMC in pH 7.4 phosphate buffered saline.
Figure 4:
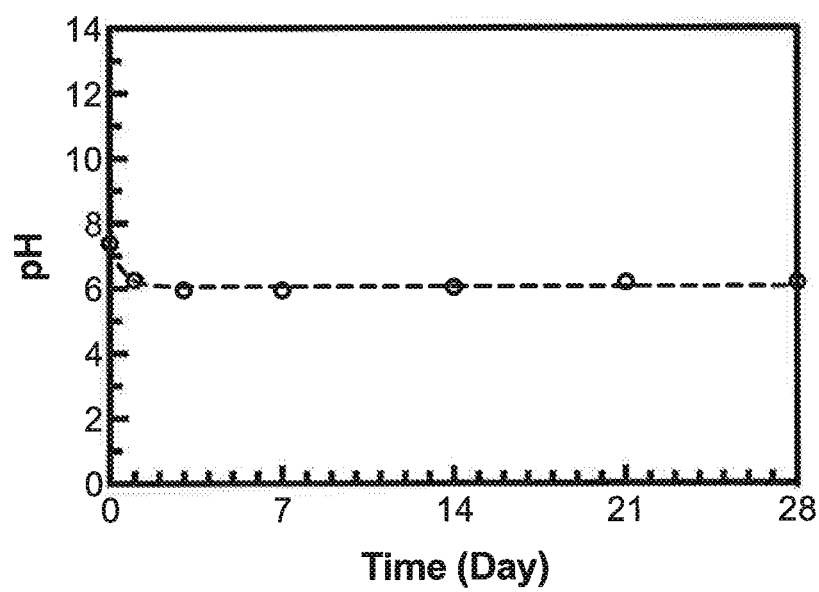
FIG. 4 is a plot showing change in pH of degradation medium (pH 7.4 phosphate buffered saline) with time during degradation of 12,750 Da PHTMC.

This copolymer was examined based on the discovery that poly(HTMC) (PHTMC) degrades via the pendant hydroxyl group attacking an adjacent carbonyl, cleaving the polymer backbone. The mechanism of PHTMC hydrolysis in an alkaline (pH>7) environment is shown in FIGS. 2A and 2B. The degradation reaction is base-catalyzed and proceeds rapidly at pH≥7, being essentially complete within 24 h. FIG. 3 shows the mass loss with time of 12,750 Da PHTMC in pH 7.4 phosphate buffered saline. The ultimate degradation products are glycerol and carbon dioxide, both of which are natural components of physiological systems. Importantly, the degradation of poly(HTMC) does not result in a significant lowering of local pH in a solution buffered to physiologic conditions. FIG. 4 shows the change in pH of degradation medium (pH 7.4 phosphate buffered saline) with time during degradation of 12,750 Da PHTMC. Accordingly, degradation of acid-sensitive drugs such as peptides and proteins, and low molecular weight drugs containing ester or lactone groups, as a result of polymer degradation is avoided.

Embodiments will be further described by way of the following non-limiting examples.

Example 1

Materials 5-benzyloxy trimethylene carbonate (BTMC) was obtained from Obiter Research LLC, USA, and trimethylene carbonate (TMC) was obtained from Leapchem, Hangzhou, China. Both were used as received. Palladium on carbon (Pd/C) (10 wt. % loading (dry basis)), palladium hydroxide on carbon (Pd(OH)$_2$/C) (20 wt. % loading (dry basis)), dimethyl sulfoxide-d6 (DMSO-d$_6$), toluene (extra dry with molecular sieves) were from Acros, USA. Tin(II) 2-ethylhexanoate (Sn(Oct)$_2$) (96% purity) was purchased from Alfa Aesar (Ward Hill, Mass., USA) and used as received. Tetrahydrofuran (THF) (high-performance liquid chromatography (HPLC) grade), methanol, ethyl acetate (EtOAc) and dichloromethane (DCM) were from Fisher Scientific, Canada, were used as received. THF, EtOAc and DCM were dried over activated 3 Å molecular sieves. Hydrogen gas (H$_2$) (99.99% purity) was from Linde Canada Ltd., Ontario, Canada.

Synthesis of poly(5-benzyloxy trimethylene carbonate-co-trimethylene Carbonate)

Poly(5-benzyloxy-trimethylene carbonate-co-trimethylene carbonate) (poly(BTMC-TMC)) copolymers of varying number average molecular weight and comonomer composition were prepared through ring-opening polymerization (ROP) using 1-butanol or 1-octanol as initiators. Three different catalysts were employed: stannous 2-ethylhexanoate (Sn(Oct)$_2$), 1,8-diazabicyclo-7-undecene (DBU), and HCl-ether. The polymerization catalyzed by stannous 2-ethylhexanoate was performed in the melt. The total monomer to catalyst molar ratio was 800:1 and the total monomer to initiator ratio was varied to achieve targeted number average molecular weights. The monomers and initiator were added into a flame dried glass ampule, the required amount of stannous 2-ethylhexanoate dissolved in toluene was added, and the sealed ampoule placed at 60° C. to melt. The melted mixture was then vortexed, purged with dry argon gas for 2 min, and placed under vacuum before heat sealing and transferring to an oven preheated to 130° C. The resulting polymers were dissolved in CH$_2$Cl$_2$ and precipitated sequentially in methanol cooled using ice.

When HCl or DBU were used as the catalyst, polymerizations were performed in solution. Prescribed amounts of TMC and BTMC were dissolved in dry dichloromethane (DCM) at a 50:50 molar ratio and concentration of 1 M to prepare compositions of 40 and 18 repeating units using DBU and HCl as catalyst, respectively. Then 1-octanol was added as an initiator. To avoid auto-initiation and initiation with water the polymerization reaction was performed under argon in flame-dried vials at room temperature using anhydrous DCM. Finally, either DBU or HCl were added to the polymerization solutions in two separate flasks at the ratio of monomer/DBU: 80 and monomer/HCl: 3. To determine the monomer conversion rate, the polymerization solution was collected at different time points. For the polymerization solutions using DBU as catalyst the reaction was quenched by adding 2 equivalents of acetic acid to catalyst at each time point.[14] Polymerization using HCl was quenched at each time point by evaporating the solvent and HCl using a flow of air over the sample following the addition of 10-fold diethyl ether as a non-solvent to completely precipitate the reacting molecules. Finally, the polymer samples were stored at −20° C. until analyzed further.

Synthesis of poly(trimethylene carbonate-co-5-hydroxy trimethylene Carbonate) (poly(TMC-HTMC))

The benzyl protecting group of poly(BTMC-TMC) was removed from the polymer backbone using a palladium-catalyzed hydrogenation. In general, 1.6 g of a mixture of Pd/C (10%) and Pd(OH)$_2$/C (20%) catalyst (1:1 mass ratio) were added into a Parr reaction vessel with 2 mL anhydrous toluene and purged with nitrogen. Next, 8 g of poly(BTMC-TMC) copolymer were first dissolved in 72 mL of THF/methanol (4/1 v/v) and transferred into the Parr vessel. The reaction mixture was purged with hydrogen gas (H$_2$) four times at 120 psi. Following purge, the vessel was pressurized to 120 psi and sealed for 24 h with stirring at room temperature. The mixture was filtered through Celite to remove the catalyst and the solvents were evaporated to give poly(TMC-HTMC). The polymer was further washed with Milli-Q water (10 mL×4) and vortexed for 2 minutes each time. The supernatant was decanted and the final polymer was freeze-dried for 2 days.

Polymer Characterization

The composition of the copolymers was calculated from the $^1$H NMR spectra obtained in DMSO-$d_6$ on a Bruker Avance 400 MHz NMR by comparing the integration of the methylene group of BTMC (O$\underline{CH_2}$C$_6$H$_5$, 4.59 ppm) with TMC (OCH$_2$$\underline{CH_2}$CH$_2$O, 1.94 ppm). GPC (Waters) was used for evaluation of the molecular weight and its molar mass dispersity ($Đ_M$). The system was equipped with a differential refractive index detector (RI) and an automatic sample injection and delivery module (Waters). THF was used as an eluent at a flow rate of 0.3 mL s$^{-1}$ at 40° C. After filtration through 0.45-micron filter, samples were injected to the column at a concentration of 4 mg mL-1. The separation was done using four columns (Waters) [4× Styragel HR 4 THF (300×4.6 mm)]. The number average molecular weight ($M_n$) and molecular weight distribution ($Đ_M$) were determined relative to linear polystyrene ($M_n$=890 to 3.28×10$^6$ g/mol) standards using Empower 2 software (Waters). The glass transition temperature ($T_g$) of the polymer samples was measured using a Mettler Toledo DSC1 system. Samples were run through two heating cycles and one cooling cycle. The heating cycles ran from −80° C. to 100° C. and the cooling cycles ran from 100° C. to −80° C. with a cooling rate of 20° C./min and a 2 min set point hold time. The $T_g$ was taken from the second heating cycle unless otherwise mentioned.

End group fidelity (α), which quantifies the number of polymer chains that incorporate the initiator, was calculated as shown in Equation 1 [17]. The terminal group ratio (τ) was calculated by dividing the peak integration at 3.67 ppm (terminal CH$_2$ on the polymer chain) by the integration of the peak at 0.9 ppm (CH$_3$ of the alcohol initiator following polymerization). If no chains were initiated by another source, such as residual water and no transesterification occurred, τ would be 1. The amount by which τ exceeds 1 represents the integration contribution from polymer chains without an attached initiator. This quantity is then halved to account for the fact that non-alcohol initiated polymer chains will have an identical terminal CH$_2$ group on both chain ends due to decarboxylation of the carbonic ester end. α is then obtained by normalizing the number of alcohol initiated polymer chains to the total number of polymer chains (initiated plus non-initiated). If τ<1, then α=τ, and $M_n$ was calculated by equation (1).

$$\tau = \frac{\frac{(I_{H2'} + I_{H3'})}{3} + \left(\frac{I_{T2'} + I_{T3'}}{4}\right)}{\frac{I_1}{3}} \quad (1)$$

If τ>1, then:

$$\alpha = \frac{1}{1 + \frac{t-1}{2}} \quad (2)$$

and $M_n$ is calculated as:

$$M_n = \left(M_{w(TMC)} \cdot \frac{I_{T2}}{2} + M_{w(HTMC)} \cdot I_{H2} + M_{wi}\right) \cdot \alpha \quad (3)$$

If τ<1, then α=τ, and $M_n$ is calculated as:

$$M_n = \left(M_{w(TMC)} \cdot \frac{I_{T2}}{2} + M_{w(HTMC)} \cdot I_{H2} + M_{wi}\right) \cdot \alpha + \\ 2 \cdot \left(M_{w(TMC)} \cdot \frac{I_{T2}}{2} + M_{w(HTMC)} \cdot I_{H2} + M_{wi}\right) \cdot (1 - \alpha) \quad (4)$$

In these equations, $M_{w(TMC)}$, $M_{w(HTMC)}$ and $M_{wi}$ are the molar mass of TMC, HTMC and initiator (either 1-octanol or 1-butanol), respectively.

Melt viscosity was measured using a Reological Visco Tech controlled stress rheometer at 25° C. and 37° C. A parallel plate stainless steel fixture with a diameter of 20 mm and a 0.5 mm plate gap was used.

Polymer Degradation

In vitro hydrolytic degradation of the copolymers was studied using ~50 mg of the copolymer (n=3 for each time point) in 4 mL of pH 7.4 phosphate buffer saline (PBS, 1×) at temperature of 37° C. for 8 weeks with gentle agitation (100 rpm). The buffer was replaced every 3 days, and at each time point samples were rinsed with Milli-Q water to remove residual salt and then dried to a constant weight on lyophilizer. Samples were assessed for weight loss, changes in molecular weight (NMR), and composition (NMR). The solution pH was also monitored to check the effect of the degradation products on the aqueous environment pH.

Drug Release

To demonstrate the potential of the P(TMC-HTMC) copolymer as an injectable sustained release drug depot, triamcinolone as an example of a low molecular weight drug with chronic therapeutic application for conditions such as intravitreal delivery for ocular inflammation and lysozyme as a model protein therapeutic were incorporated into P(TMC-HTMC) and released into PBS at 37° C. All release data are plotted as the mean±the standard deviation of triplicate samples.

Triamcinolone Release

Triamcinolone incorporation was achieved by two methods. In the first method, 1 or 5% w/w of triamcinolone with respect to P(TMC-HTMC) were dissolved in anhydrous THF. In detail, 400 mg of P(TMC-HTMC) was mixed with 1 or 5% w/w of triamcinolone and co-dissolved in 4 mL of THF, the solvent was evaporated by N$_2$ flow in fume hood for 1 day and the polymer/drug mixture was further freeze-dried on a lyophilizer for three days. In the second method, triamcinolone was first ground and sieved through 45 µm sieves and then directly mixed with P(TMC-HTMC) without using solvents. Bright-field images of triamcinolone particles were recorded using an inverted light microscope (Hund Wetzlar model Wilovert S; Wetzlar, Germany) with a mounted Leica camera (model DFC320) at 10× or 20× magnification and analyzed using ImageJ 2.0 software for a quantitative assessment of particle size distribution and DSC was used to determine whether triamcinolone has been uniformly dispersed in polymer.

For the release study, each 4 mL of glass vial was filled with ~50 mg of polymer/drug mixture and 3 mL of PBS was added (n=3 for each time point). At each sampling period the PBS was removed and replaced with fresh solution. The collected PBS buffer was stored in the refrigerator for HPLC analysis. The released samples were filtered through a 0.45 µm acetate cellulose filter and the triamcinolone content was measured via HPLC (Agilent Technologies 1260 Infinity with an Agilent Eclipse Plus c18 3.5 µm (4.6×100 mm) column using 215 nm UV absorbance detection (1260 VWD VL+)). Mobile phase: A=20% acetonitrile in Milli-Q $H_2O$ with 0.1% v/v trifluoroacetic acid, B=50% acetonitrile in Milli-Q $H_2O$ with 0.1% v/v trifluoroacetic acid; Injection volume: 20 µL, Gradient: at 0 min 0% B, at 6 min 30% B, Column wash: at 8 min 0% B; Flow rate: 1.0 mL/min. A calibration curve was previously prepared using standard solutions of triamcinolone in PBS with concentrations ranging from 0.025 to 0.15 mg/mL. The concentration of triamcinolone released from polymer at each time point was converted to a mass of triamcinolone, which was then used to calculate the cumulative amount released. The data was then plotted as the mass % of triamcinolone released versus time by dividing the cumulative amount released by the total mass of triamcinolone released from the copolymer.

Protein Release

Lysozyme (98%, Sigma-Aldrich) was used as a model protein drug. Protein particles were prepared by dissolving lysozyme and trehalose in pH 7.4 PBS at a lysozyme: trehalose ratio of 98:2 (w/w) to achieve a total lysozyme concentration of 5% w/w. The solution was frozen in liquid nitrogen and lyophilized at −50° C. and 100 mbar. The resulting dry powder was sieved to yield <45 µm diameter particles. The lyophilized particles were then mixed by hand into the copolymer using a spatula after first pre-heating the copolymer to 37° C. to yield a suspension of the particles. The polymer suspension was loaded into a 1 mL syringes then ~100 mg injected through an 18-gage needle into the bottom of a 1 mL glass vial. The exact weight of the injected suspension in each vial was measured and recorded. The glass vial was filled with 1 mL of pH 7.4 PBS containing 0.02% Tween 20 and 0.02% sodium azide. The samples were then agitated in a thermomixer with horizontal shaking at 300 rpm while being maintained at 37° C. At specified time points, the release medium was completely removed and replaced with fresh medium. The lysozyme concentration in the releasate was measured using a bicinchoninic acid (BCA) protein assay kit from Thermo Scientific. Protein particle loadings of 1 and 2% w/w were examined along with three copolymer compositions: 1-octanol initiated 1200 Da copolymer, 1-octanol initiated 1900 Da copolymer, and 1-butanol initiated 1900 Da copolymer. For each copolymer, the HTMC content was 30 mol %.

Results

Polymer Synthesis

Three different catalysts were examined for the copolymerization of TMC with BTMC, with the objective of obtaining controllable molecular weight, a TMC:BTMC monomer ratio equal to that of the feed ratio, a random comonomer sequence along the polymer backbone, and high end group fidelity (α). The catalysts chosen were HCl-ether, DBU, and $Sn(Oct)_2$. Each of these catalysts reportedly functions differently. HCl-ether activates the monomer making it more susceptible to nucleophilic attack by the hydroxyl group on the initiator or the growing chain end. In contrast, DBU is believed to activate both the hydroxyl group on the chain end, increasing its nucleophilicity. Finally, $Sn(Oct)_2$ is generally considered to act in a coordination-insertion manner, in which the Sn group becomes attached to the growing end of the polymer chain and coordinates with the carbonyl of a carbonate monomer, ultimately causing it to be inserted between the Sn group and the rest of the polymer chain.

Figure 5:
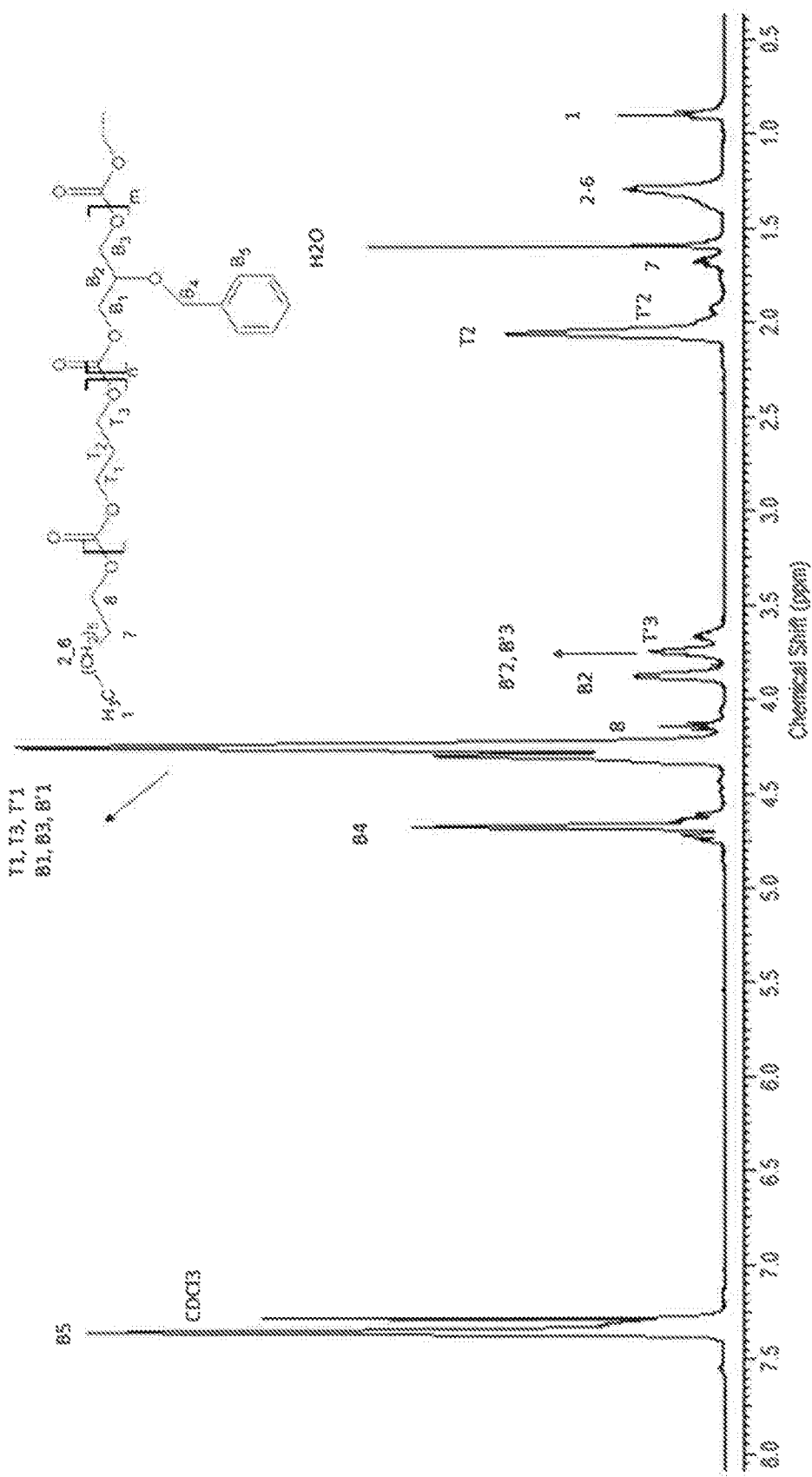
FIG. 5 shows a $^1$H NMR spectrum for poly(TMC-co-BTMC) prepared using HCl-ether as a catalyst and 1-octanol as an initiator, obtained in $CDCl_3$, wherein peak assignments are shown relative to the designations in the copolymer structure given, and peaks labelled with an apostrophe are related to the end units of the copolymer chain.
Figure 6:
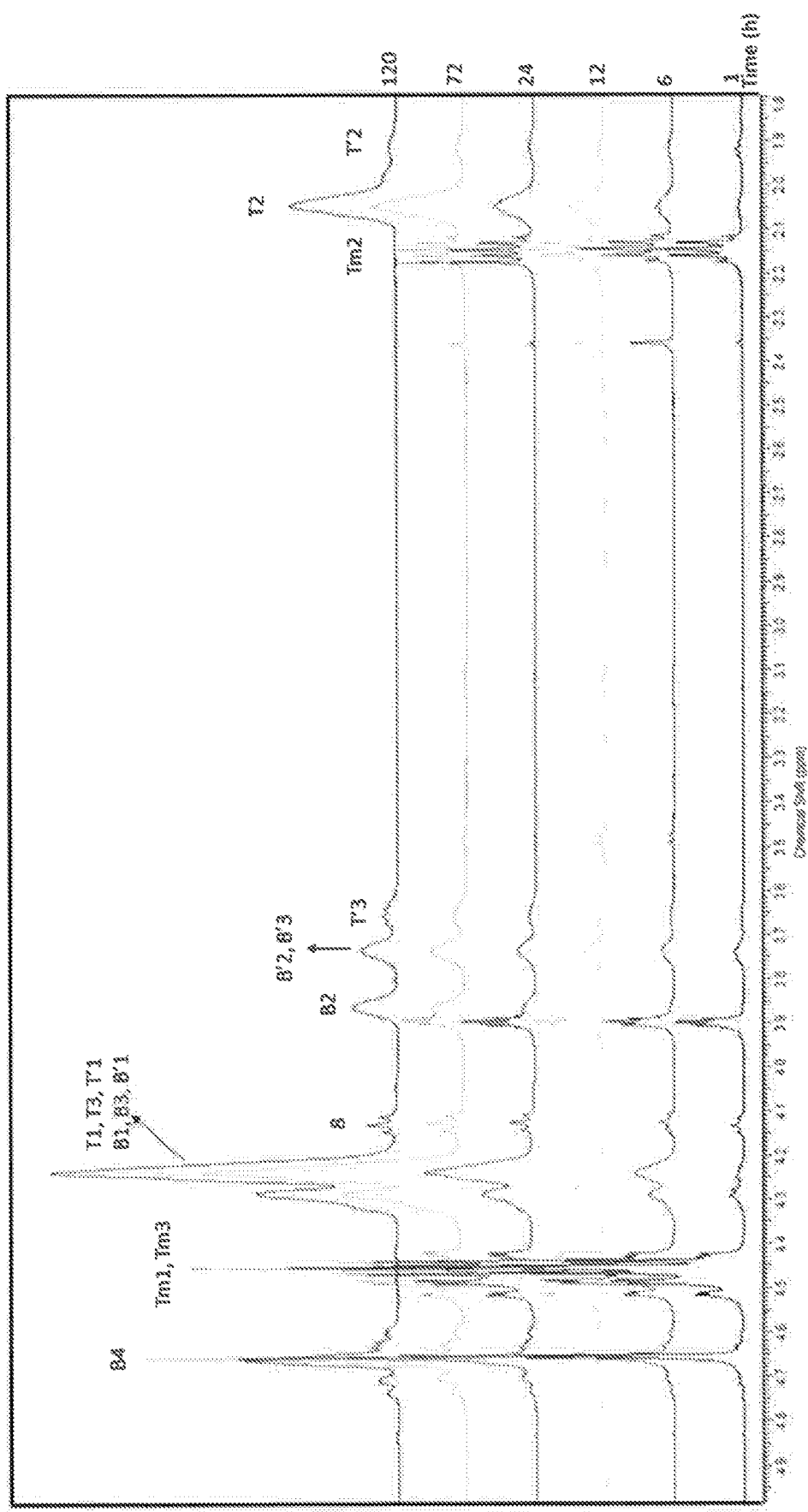
FIG. 6 is a diagram showing stacked $^1$H NMR spectra of TMC and BTMC conversion with time during copolymerization, wherein the initiator was 1-octanol and the catalyst was HCl-ether, and the spectra were obtained in $CDCl_3$.

As a preliminary assessment, the polymerization kinetics were followed by monitoring monomer conversion with time for each catalyst via $^1H$ NMR spectroscopy. In these experiments, 1-octanol was used as the initiator, while an equimolar ratio of TMC and BTMC was used in the feed. A representative $^1H$ NMR spectrum of a resulting copolymer is given in FIG. 5, obtained in $CDCl_3$, wherein peak assignments are shown relative to the designations in the copolymer structure given, and peaks labelled with an apostrophe are related to the end units of the copolymer chain, and stacked $^1H$ NMR spectra showing the monomer conversion with time is shown in FIG. 6.

TMC conversion was calculated by comparing the area under the T2 peak (δ=2.06 ppm) for the growing PTMC chain with the area under the $T_m2$ peak corresponding to the TMC monomer (δ=2.16 ppm). To calculate the BTMC conversion rate, the area under the B1 and B3 peaks (δ=4.16-4.38 ppm) corresponding to incorporated PBTMC was compared to the area under the B5 peak (δ=7.36 ppm) for the BTMC monomer.

Figure 7A:
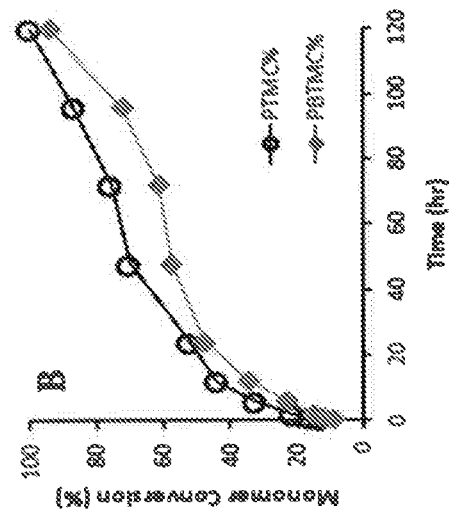
FIGS. 7A-7C are plots showing monomer conversion versus time for the copolymerization of TMC and BTMC using different catalysts: (7A) $Sn(Oct)_2$, 130° C.; (7B) HCl-ether, room temperature and (7C) DBU, room temperature.
Figure 7B:
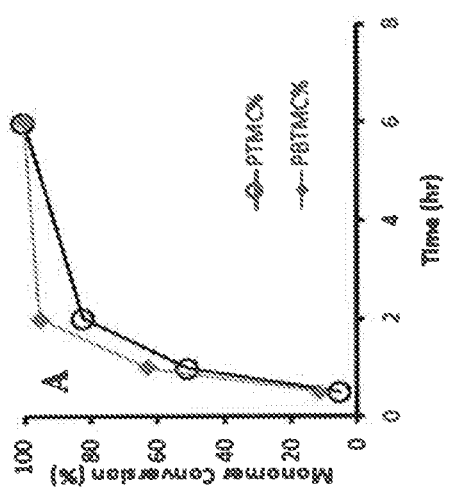
Figure 7C:
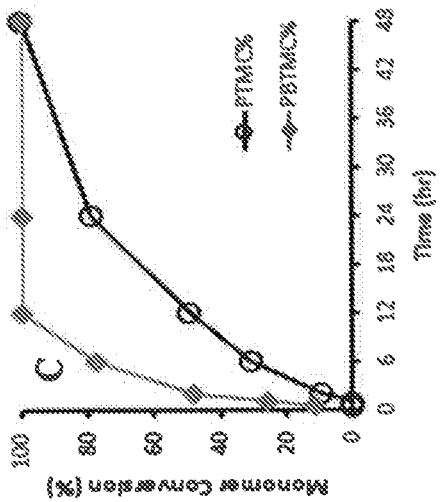

FIGS. 7A-7C show the monomer conversion versus time in the presence of selected catalysts. With $Sn(Oct)_2$ as catalyst and undertaking the ring-opening polymerization in the melt, TMC and BTMC polymerized at nearly the same rate with BTMC polymerizing slightly faster than TMC (FIG. 7A). When copolymerized in solution using HCl-ether as the catalyst, again both monomers were incorporated into the copolymer at nearly the same rate, with TMC reacting slightly faster (FIG. 7B). The polymerizations however, proceeded much more slowly, reaching complete conversion in 120 h, in contrast to the complete conversion within 6 h found using $Sn(Oct)_2$ in a melt copolymerization at 130° C. Thus, with both $Sn(Oct)_2$ and HCl-ether, random copolymers were formed. In contrast, with DBU as catalyst, blocky copolymers (i.e., copolymers that are not strictly block copolymers, but which have a low amount of the one comonomer in a region of the other comonomer in much greater amount) were formed as BTMC polymerized much faster than TMC, reaching complete conversion in 12 hours while at that time, TMC conversion was only 50% (FIG. 7C).

As random copolymers were desired, subsequent copolymerizations were conducted using either HCl-ether or $Sn(Oct)_2$ as the catalyst to form copolymers of varying molecular weight and comonomer composition. The properties of the resulting copolymers are given in Table 1. End group fidelity was better when $Sn(Oct)_2$ was used as the catalyst, and increased as the number of moles of BTMC in the feed composition decreased for either catalyst. Reasonably good control over molecular weight was also obtained with either catalyst.

TABLE 1

Poly(TMC-BTMC) properties with respect to comonomer feed composition and catalyst.

| Initiator (I) | Catalyst | Feed mols BMTC | Target $M_n$ (Da) | mols BMTC | $M_n$ (Da) | α |
|---|---|---|---|---|---|---|
| butanol | HCl | 50 | 1005 | 49 | 609 | 56.2 |
| butanol | HCl | 28.6 | 1000 | 30 | 738 | 74.5 |
| butanol | HCl | 50 | 2866 | 50.2 | 1920 | 70.6 |
| butanol | HCl | 27.8 | 2441 | 27.3 | 1407 | 61.7 |
| octanol | HCl | 30 | 1469 | 29.6 | 942 | 73.7 |
| octanol | HCl | 50 | 2922 | 50.6 | 1694 | 63 |

TABLE 1-continued

Poly(TMC-BTMC) properties with respect to comonomer feed composition and catalyst.

| Initiator (I) | Catalyst | Feed mols BMTC | Target $M_n$ (Da) | mols BMTC | $M_n$ (Da) | α |
|---|---|---|---|---|---|---|
| octanol | HCl | 27.8 | 2497 | 24.7 | 1650 | 70.7 |
| octanol | Sn | 50 | 2923 | 48.9 | 3458 | 80 |
| octanol | Sn | 30 | 2328 | 29.1 | 2541 | 89.8 |
| octanol | Sn | 20 | 1362 | 19.6 | 1298 | 93.7 |
| octanol | Sn | 10 | 1256 | 9.8 | 1250 | 97.6 |
| octanol | Sn | 0 | 1150 | 0 | 1150 | 100 |

Following copolymerization, the polymers were de-benzylated to convert the BTMC repeating units to HTMC repeating units, and then purified by precipitation. The resulting copolymers and their properties are given in Table 2. In general, the end group fidelity increased upon debenzylation and purification. This result is attributed to the loss of low molecular fractions during the purification procedure. All the resulting copolymers had low glass transition temperatures and were amorphous. The glass transition temperature of the resulting copolymers increased as molecular weight increased, as would be expected. For copolymers of the approximately the same molecular weight (those of $M_n$ between 1150 and 1207 Da), the glass transition temperature increased as the amount of HTMC in the copolymer increased, reflective of the influence of hydrogen bonding provided by the pendant hydroxyl group of the HTMC on the glass transition temperature. The initiator used had little influence on the glass transition temperature. For example, for the copolymers with a molecular weight of approximately 1800 Da and a monomer composition of 50% HTMC, the glass transition temperature was −23° C., regardless of whether 1-butanol or 1-octanol was used as the initiator.

TABLE 2

Properties of TMC-HTMC copolymers prepared via debenzylation of copolymers listed in Table 1.

| Initiator (I) | Catalyst | mols HMTC | $M_n$ (Da) | $T_g$ (° C.) | α |
|---|---|---|---|---|---|
| butanol | HCl | 46 | 613 | −50 | 75 |
| butanol | HCl | 29 | 780 | −39 | 94.5 |
| butanol | HCl | 50 | 1774 | −23 | 90 |
| butanol | HCl | 26.3 | 1463 | −25.6 | 86 |
| octanol | HCl | 27 | 1165 | −35.2 | 100 |
| octanol | HCl | 30 | 1600 | −24.5 | 83 |
| octanol | HCl | 48.7 | 1810 | −23 | 95 |
| octanol | Sn | 49.5 | 2630 | −15.9 | 76 |
| octanol | Sn | 29.7 | 2350 | −23.9 | 74 |
| octanol | Sn | 21 | 1180 | −38 | 100 |
| octanol | Sn | 11 | 1207 | −42 | 100 |
| octanol | Sn | 0 | 1150 | −45 | 100 |

Liquid polymers can be readily injected by hand through standard gauge needles provided they have a viscosity less than about 100 Pa·s. The viscosities of the copolymers can be adjusted by choice of initiator, by the number of HTMC repeating units, as well as molecular weight (Table 3). All the copolymers examined have a viscosity below 100 Pa·s at 37° C. (Table 3).

TABLE 3

Viscosities (η) of P(TMC-HTMC)

| Initiator | HTMC (%) | Mn (Da) | η (Pa · s, 25° C.) | η (Pas · s, 37° C.) |
|---|---|---|---|---|
| 1-butanol | 30 | 780 | 8.8 | 3.2 |
| 1-octanol | 30 | 1600 | 150 | 41 |
| 1-butanol | 30 | 1463 | 112.7 | 30.7 |

In Vitro Degradation

Figure 8:
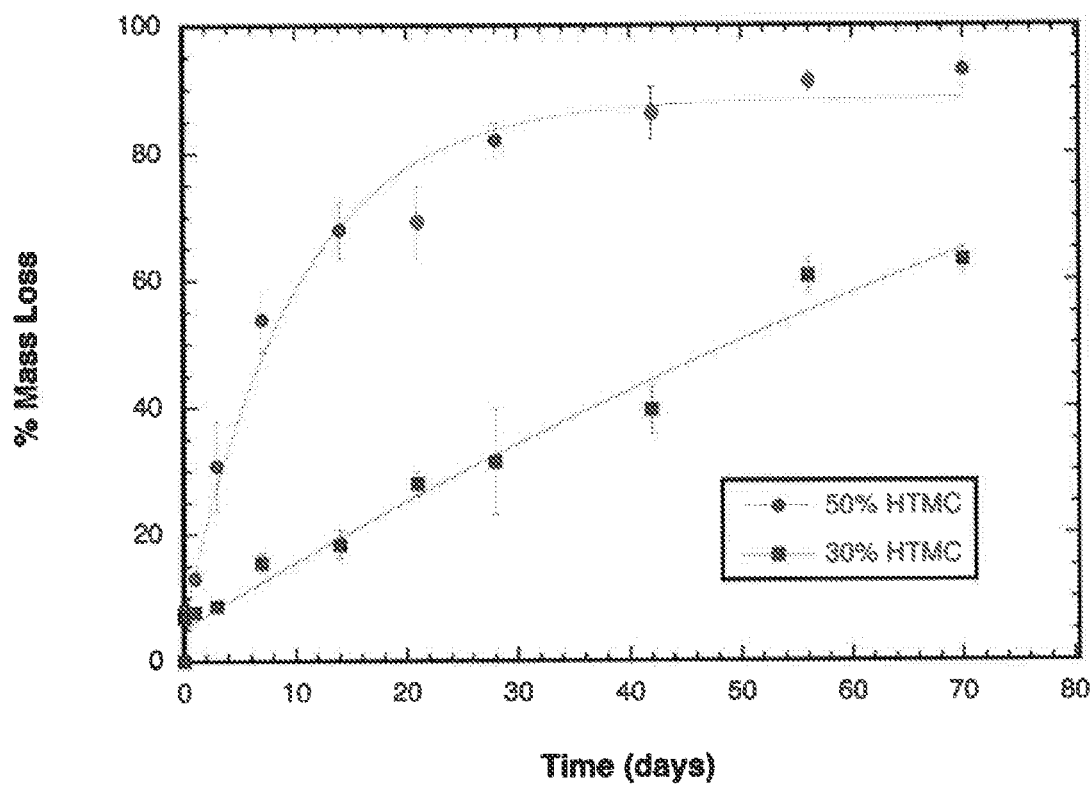
FIG. 8 is a plot showing influence of HTMC composition of copolymer on its in vitro degradation, with polymer properties: $M_n \approx 2500$ Da, initiator (I)=1-octanol.

In vitro degradation studies were undertaken in PBS under mild agitation. The degradation rate of the copolymer under these conditions was dependent on monomer composition (FIG. 8), copolymer molecular weight (FIG. 9), and the nature of the initiator used (FIG. 10). Of these factors, the HTMC composition had the greatest influence on the copolymer degradation rate (FIG. 8, polymer properties: $M_n \approx 2500$ Da, I=1-octanol). At a given molecular weight and initiator (I), degradation was markedly faster for copolymers possessing 50% HTMC versus those containing 30% HTMC; copolymers possessing 50% HTMC lost greater than 60% of their initial mass before 14 days while copolymers possessing 30% HTMC required 56 days to reach approximately the same extent of mass loss. The rate of mass loss also decreased as the extent of mass loss increased beyond about 70% for the copolymer possessing 50% HTMC, while the rate of mass loss remained nearly constant for the copolymers possessing 30% HTMC.

Figure 9:
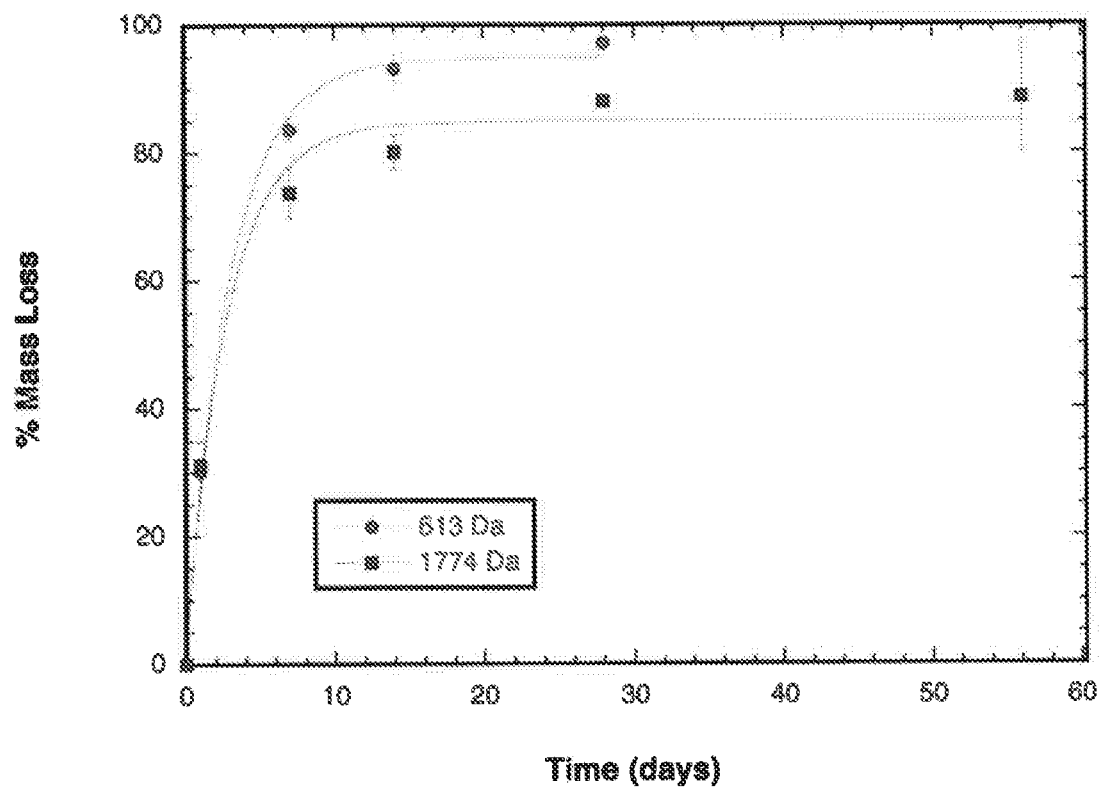
FIG. 9 is a plot showing influence of copolymer number average molecular weight on its in vitro degradation, with polymer properties: 50% HTMC, I=1-butanol.
Figure 10:
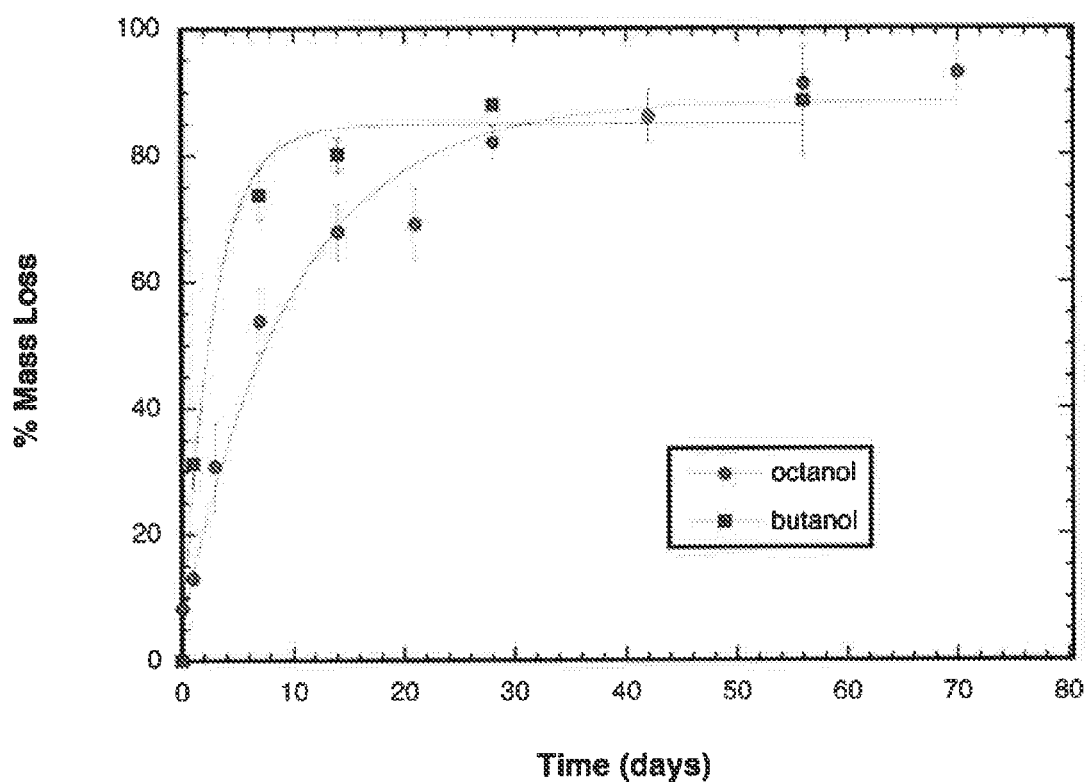
FIG. 10 is a plot showing influence of initiator used to prepare the copolymer on its in vitro degradation, with polymer properties: $M_n \approx 1800$ Da, 50% HTMC.

At a given comonomer composition (50%) and initiator (1-butanol), the in vitro degradation rate decreased as the number average molecular weight of the copolymer increased (FIG. 9, polymer properties: 50% HTMC, I=1-butanol). The difference in the degradation rate with respect to copolymer molecular weight, however, was not as pronounced as observed when the comonomer composition was varied. A difference in molecular weight of nearly three times only resulted in a difference in total mass loss of approximately 10% by 28 days, by which time each copolymer had lost at least 85% of its initial mass. Again, for both copolymers, the rate of degradation decreased as the extent of mass loss increased beyond approximately 70%.

Finally, at a given molecular weight (~1900 Da) and comonomer composition (50% HTMC), the rate of degradation was greater for copolymers prepared using 1-butanol as the initiator versus those prepared using 1-octanol (FIG. 10, polymer properties: $M_n \approx 1800$ Da, 50% HTMC). The copolymers prepared using 1-butanol reached greater than 70% mass loss by 7 days, while those prepared using 1-octanol reached the same extent of mass loss by approximately 21 days. Furthermore, as noted above, for both copolymers, the rate of degradation decreased as the extent of mass loss increased beyond approximately 70%.

Figure 11A:
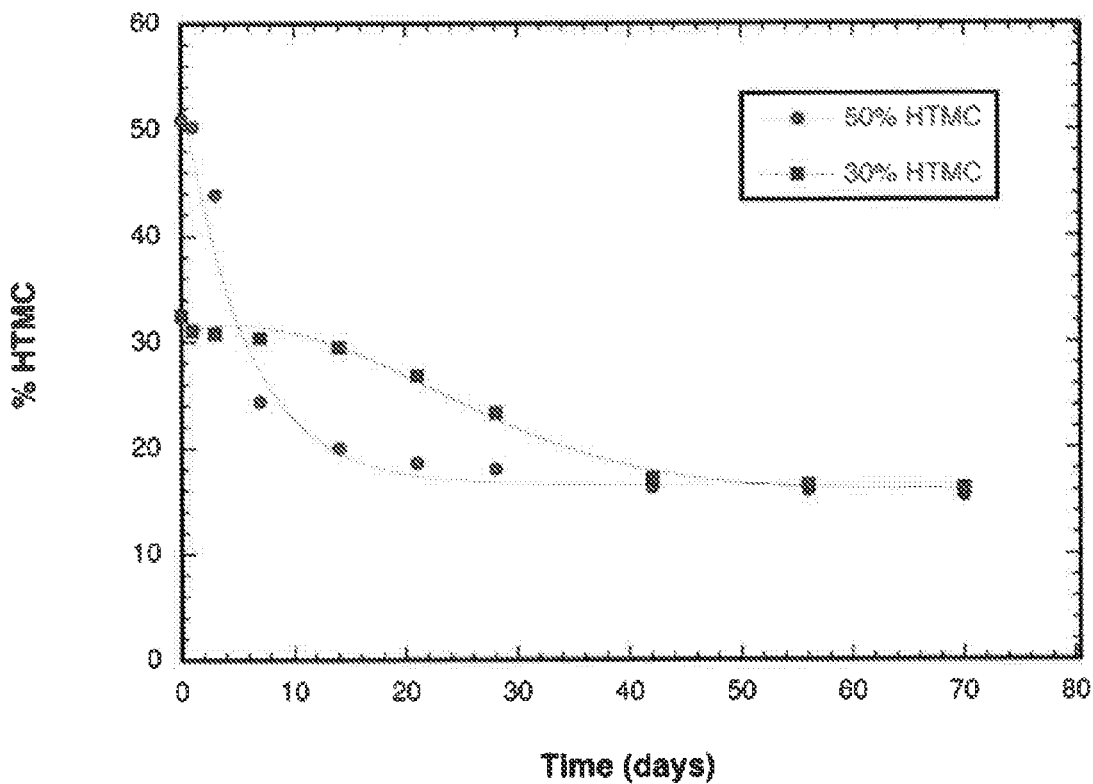
FIGS. 11A-11C are plots showing change in copolymer HTMC monomer content with time during in vitro degradation as a function of: (11A) initial monomer composition ($M_n \approx 2500$ Da, I=1-octanol), (11B) initial copolymer molecular weight (I=1-butanol), and (11C) initiator used to prepare the copolymer ($M_n \approx 1800$ Da).
Figure 11B:
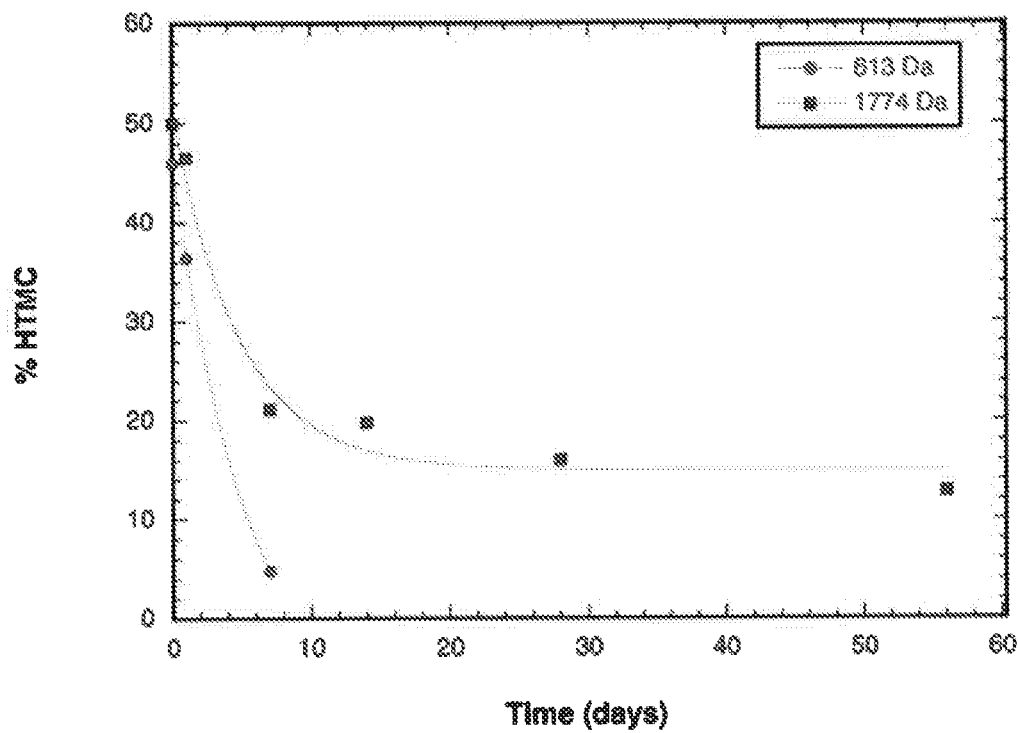
Figure 11C:
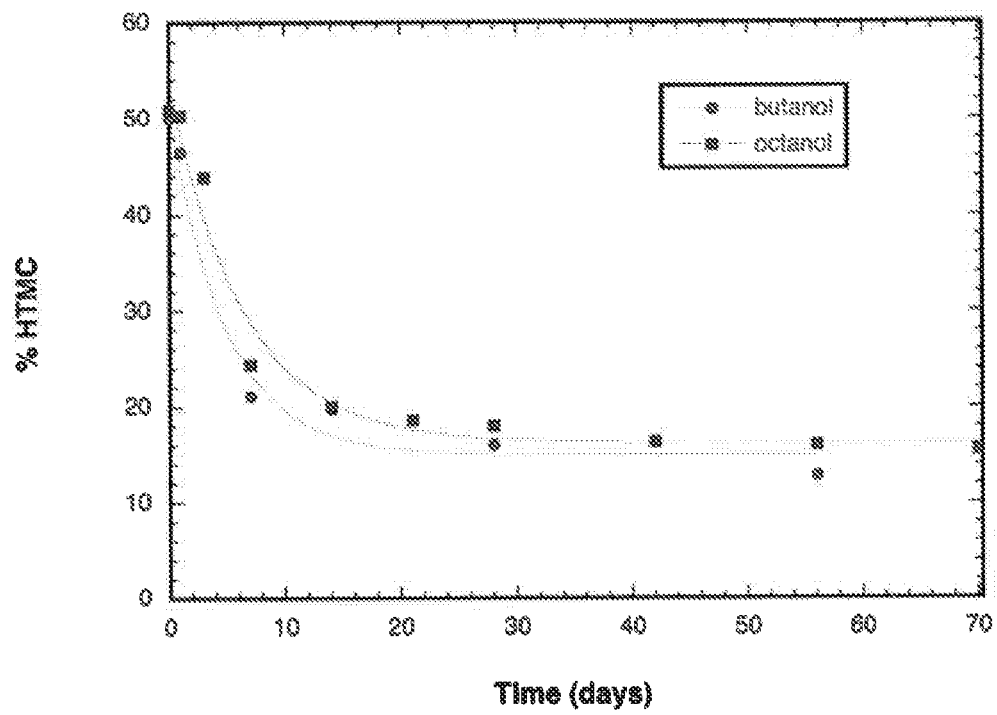

To obtain further insight into the mechanism of degradation for these copolymers, the monomer composition and number average molecular weight ($M_n$) of the remaining copolymer were measured with time. The change in HTMC content of the copolymers with time as a function of initial copolymer monomer composition, molecular weight, and initiator used is given in FIGS. 11A-11C (for FIG. 11A, initial monomer composition ($M_n \approx 2500$ Da, I=1-octanol); FIG. 11B initial copolymer molecular weight (I=1-butanol); and FIG. 11C, initiator used to prepare the copolymer ($M_n \approx 1800$ Da), while the change in the $M_n$ is given in FIG. 12.

The HTMC content of the copolymer mass that remains as a separate phase from the buffer medium decreased with time for all cases. This result is a product of the hydrolytic resistance of the TMC carbonate linkage and the rapid cleavage of the carbonate linkage induced by the pendant hydroxyl group of the HTMC monomer (FIG. 3). Except for the very low molecular weight (613 Da), butanol initiated copolymer containing 50% HTMC initially, all the other polymers reached a plateau amount of HTMC within the remaining copolymer of 15-16%.

Figure 12A:
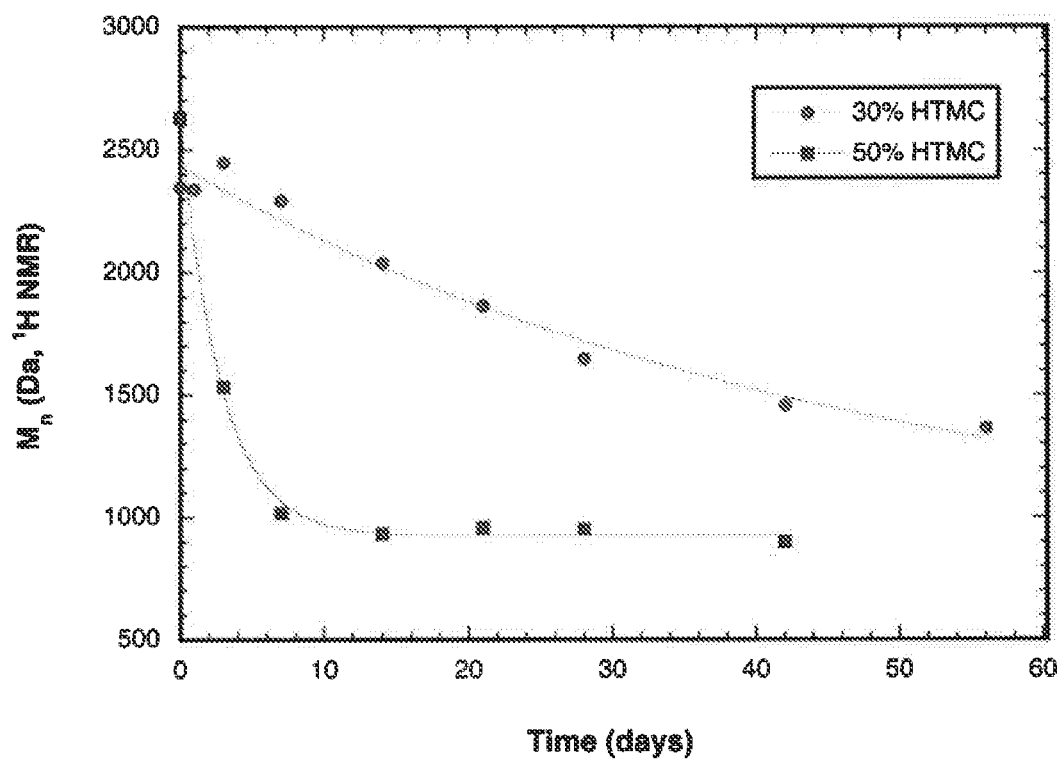
FIGS. 12A and 12B are plots showing change in copolymer $M_n$ with time during in vitro degradation as a function of: (12A) initial monomer composition (I=1-octanol), and (12B) initiator used to prepare the copolymer (50% HTMC).
Figure 12B:
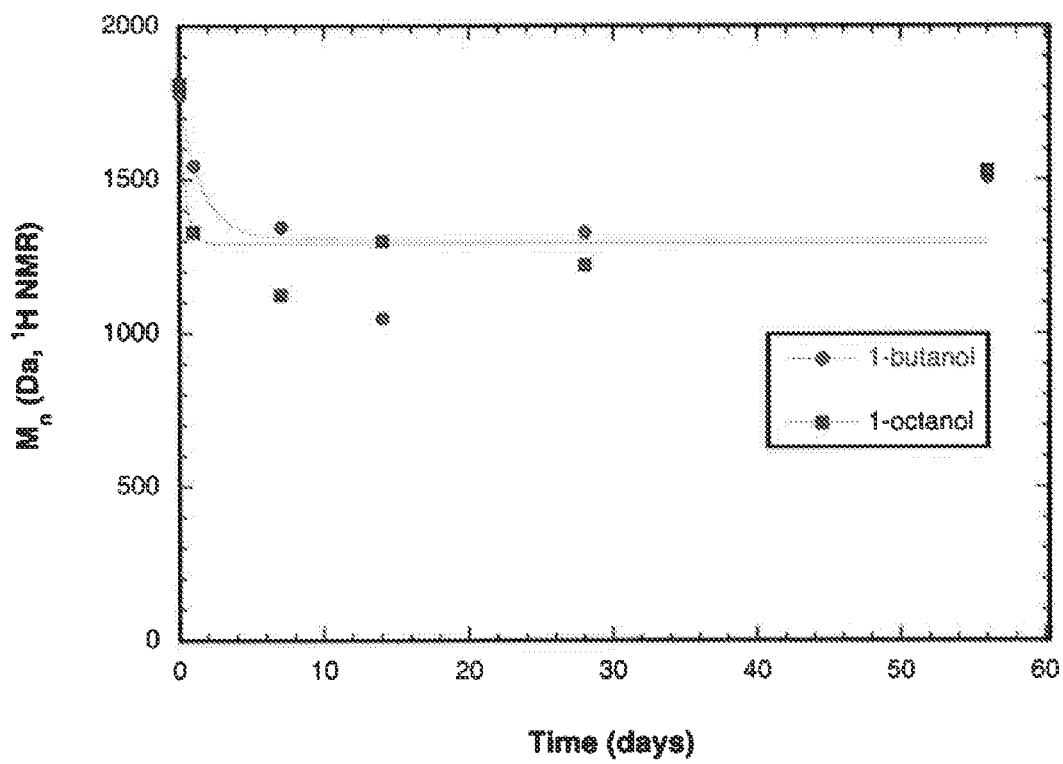

In a similar fashion as the change in HTMC content with time, the copolymer molecular weight decreased with time in an exponential decay fashion, reaching a plateau value that was consistently about 1000-1300 Da (FIGS. 12A and 12B). The rate of decrease in $M_n$ with time increased with increasing HTMC content for a given initiator and molecular weight (FIG. 12A, initial monomer composition (I=1-octanol)), and as the hydrophobicity of the initiator decreased for a given molecular weight and HTMC content (FIG. 12B, initiator used to prepare the copolymer (50% HTMC)).

These findings are explained as follows. The rapid mass loss is due to loss of HTMC repeating units along the polymer backbone; the greater number of HTMC units per chain is reflected in a greater number of potential bond cleavage events. As bonds are cleaved the M and HTMC content decreases. If a bond cleavage yields a product that is water soluble, then that product is lost to the water phase. The water solubility of a degradation product is also greater if it contains more HTMC. This loss is rapid at the surface but is slower in the bulk of the sample as the degradation products need to diffuse through the polymer to reach the surface. The decrease in degradation rate observed is due to the HTMC content of the remaining polymer chains having been reduced to the extent where their aqueous solubility is low. At a given molecular weight, the initiator used has no effect on the change in HTMC content with time; this result suggests that the mass loss in this case is primarily affected by the water solubility of the degradation product, which is higher for the butanol than for the octanol. This finding also supports the conclusion that the decrease in degradation rate is due to the reduction in water solubility of the degradation products.

Figure 13:
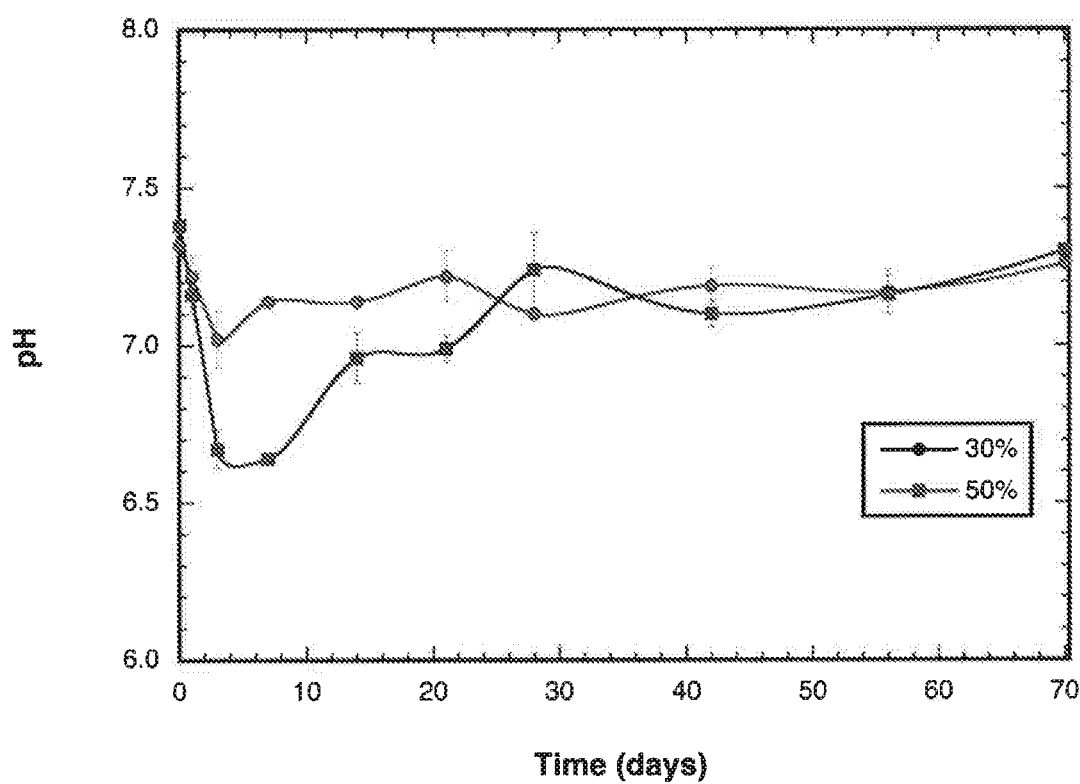
FIG. 13 is a plot showing pH of degradation medium during in vitro degradation of 1900 Da P(TMC-HTMC) of varying HTMC content (30 and 50%) in PBS.

An important consideration for the potential utility of these polymers is the change in pH of the degradation medium induced by the generation of degradation products. For these copolymers, one of the degradation products is carbon dioxide, which in water is converted to carbonic acid. The pH of the PBS was therefore monitored with time during degradation for the copolymers initially containing 30 and 50% HTMC, initiated with 1-octanol, and which had an initial molecular weight of approximately 1900 Da. For the more rapidly degrading copolymer (50% HTMC), the buffer pH decreased initially, to 6.65 by day 7, then rose back up to neutral pH by day 14 (FIG. 13). The decrease in pH corresponds to the period of most rapid mass loss (FIG. 8) and decrease in HTMC content of the copolymer (FIG. 11A), and therefore is attributed to the formation of carbonic acid by the carbon dioxide formed. It is notable, however, that the pH of the phosphate buffered saline degradation medium was only mildly acidic and that the duration of the acidic conditions was not prolonged. The pH of the medium surrounding the more slowly degrading 30% HTMC copolymer always remained neutral, a result of the reduced amount of carbon dioxide generated per time.

In summary, the in vitro degradation of random copolymers of TMC and HTMC can be readily tailored by adjusting the amount of HTMC in the copolymer, the initial molecular weight of the copolymer, and the initiator used in its preparation. Specifically, the degradation rate increases as the amount of HTMC incorporated into the copolymer increases, as the molecular weight of the copolymer decreases, and as the hydrophobicity of the initiator decreases. Moreover, the degradation yields products such as glycerol and carbon dioxide that are reasonably expected to be non-toxic in vivo, and which will not cause a substantive change in tissue pH upon implantation in vivo.

In Vitro Release of Triamcinolone

Triamcinolone was loaded into 1-octanol initiated, ~2500 Da P(TMC-HTMC) having both 50% HTMC and 30% HTMC composition. The drug was loaded into the copolymer by two methods. In the first, triamcinolone was co-dissolved with poly(TMC-HTMC) in tetrahydrofuran (THF), the polymer/drug mixture was subsequently dried in a fume hood first and then freeze-dried until a constant weight was obtained. Considering the potential toxicity of residual organic solvents, in the second method triamcinolone was first ground and sieved through 45 µM sieves and then mixed directly with the copolymers. To assess the nature in which the triamcinolone was dispersed within the copolymer, the glass transition temperature of the copolymers was measured before and after triamcinolone incorporation by each method. The results are given in Table 4. The glass transition temperature ($T_g$) of the P(TMC-HTMC) decreased significantly when the drug was loaded by co-dissolution, while by direct mixing the $T_g$ only decreased slightly. When incorporated by the co-dissolution method, the decrease in $T_g$ arises due to a plasticization effect induced by the molecularly dispersed triamcinolone, while by direct mixing, the drug is mainly physically and only partially dissolved in the surrounding copolymer.

TABLE 4

Influence of triamcinolone incorporation method on the glass transition temperature of the P(TMC-HTMC) used. In each case of triamcinolone incorporation, 5% w/w of triamcinolone was loaded into the polymer.

| Polymer HTMC content (%) | triamcinolone incorporation | $T_g$ (° C.) |
|---|---|---|
| 30 | none | −21.3 |
| 30 | co-dissolved | −27.2 |
| 30 | direct mixing | −23.4 |
| 50 | none | −16.4 |
| 50 | co-dissolved | −22.0 |
| 50 | direct mixing | −16.8 |

Figure 14:
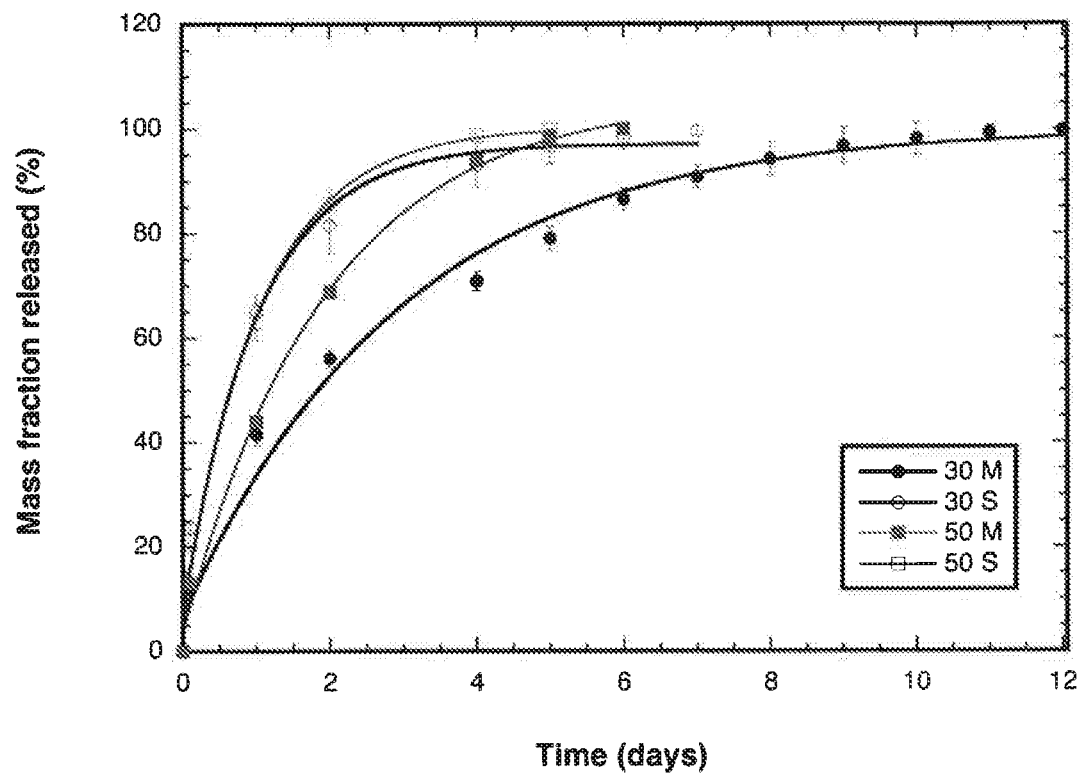
FIG. 14 is a plot showing cumulative release of triamcinolone from 2500 Da P(TMC-HTMC) into PBS (pH 7.4) at 37° C.; in the legend, 30 and 50 refer to 30% and 50% HTMC in the copolymer, while M and S refer to triamcinolone loading by direct mixing or co-dissolution in THF, respectively, and the loading of triamcinolone in each case was 1% w/w.

The in vitro release rate of the triamcinolone from the copolymer varied with the manner in which the drug was incorporated into the copolymer and the composition of the copolymer. FIG. 14 shows cumulative release of triamcinolone from 2500 Da P(TMC-HTMC) into PBS (pH 7.4) at 37° C. In the legend, 30 and 50 refer to 30% and 50% HTMC in the copolymer, while M and S refer to triamcinolone loading by direct mixing or co-dissolution in THF, respectively. The loading of triamcinolone in each case was 1% w/w. For each time point shown in FIG. 14, the triamcinolone concentration in solution was less than 10% of its saturation concentration at 25° C. of 80 mg/L, and so near infinite sink conditions could be assumed to have been maintained during the release. When incorporated via the co-dissolution method (indicated by S in the legend in FIG. 14), the release of triamcinolone did not vary with the copolymer composition. This release behaviour is consistent with the drug being molecularly dispersed throughout the copolymer and thus being released initially principally by diffusion through the copolymer. Given the differences in copolymer glass transition temperature, it would have been expected that release from the 50% HTMC copolymer would have been slower, as a solute's diffusion coefficient within a polymer increases as the glass transition temperature decreases. That the release rates were similar is attributed to the increased water uptake of the 50% HTMC copolymer, due to its greater hydrophilicity. The increased water uptake would result in a greater overall polymer/water interfacial area for diffusional transport as well as a greater degree of plasticization of the copolymer, causing a greater decrease in its $T_g$.

Significantly slower release was obtained when the drug was loaded into the copolymers as solid particles. Moreover, in this situation, the copolymer HTMC content influenced the rate of drug release. For the copolymer containing 50% HTMC, triamcinolone release was complete at day 6 whereas complete triamcinolone release required 12 days for the 30% HTMC copolymer. The release mechanism in this case is considered to proceed with the drug first dissolving from the crystalline particle into the polymer, followed by diffusion through the polymer to an aqueous medium/polymer interface. The copolymer composition would affect both the dissolution step, by influencing the drug solubility in the copolymer, as well as the diffusion phase by influencing the drug diffusion coefficient in the copolymer, as described above. Thus, release of a low molecular weight compound can be readily manipulated by adjusting the means in which it is incorporated into the copolymer as well as by adjusting the composition of the copolymer used.

In Vitro Release of Lysozyme as a Model Protein Therapeutic

Lysozyme was chosen as a model therapeutic protein because its molecular weight (14 kDa) and its isoelectric point (11) are within the range of many growth factors. To simulate formulation conditions, lysozyme was co-lyophilized with trehalose as a cryoprotectant in pH 7.4 PBS. The particles obtained after lyophilization were then ground and sieved to less than 45 μm and then loaded at either 1 or 2% (w/w) into 1800 Da P(TMC-HTMC) with an HTMC content of 30% through physical mixing. The suspensions thus prepared were then injected into the bottom of glass vials and PBS added.

For this type of formulation, the protein released is influenced by a combination of mechanisms: the rate at which the copolymer degrades and the ability of the copolymer phase to become hydrated. The release process has been postulated to occur as follows. Upon contact with the release medium, particles resident at the surface, and those particles in contact with them, dissolve and diffuse into the release media. This phase of release is referred to as the burst effect. The burst effect is low when low particle loadings are used. Water from the surrounding medium also dissolves into, and diffuses through, the polymer matrix until it encounters a polymer-enclosed drug particle. At the particle/polymer interface, the water dissolves a portion of the particle to form a saturated solution. An activity gradient is generated between the saturated solution and the surrounding aqueous medium. The activity gradient draws water into the polymer to generate an osmotic pressure equal to the osmotic pressure of the saturated solution at the particle/polymer interface. As a result of the low molecular weight of the polymer, water is forced into the polymer region surrounding the capsules, generating superhydrated regions, wherein the water concentration is higher than that obtained from fully hydrating the polymer in the absence of the encapsulated particles. The water forced into the surrounding polymer forms "zones of excess hydration". These zones eventually overlap to form a continuous pathway extending to the surface. The dissolved solutes are transported through this superhydrated region to the surface. At the same time, the polymer is degrading. The degradation of the polymer increases the rate at which water can penetrate the polymer, increasing the water content of the superhydrated regions as well as reduces the distance over which a dissolved solute must transport in order to be released.

Figure 15:
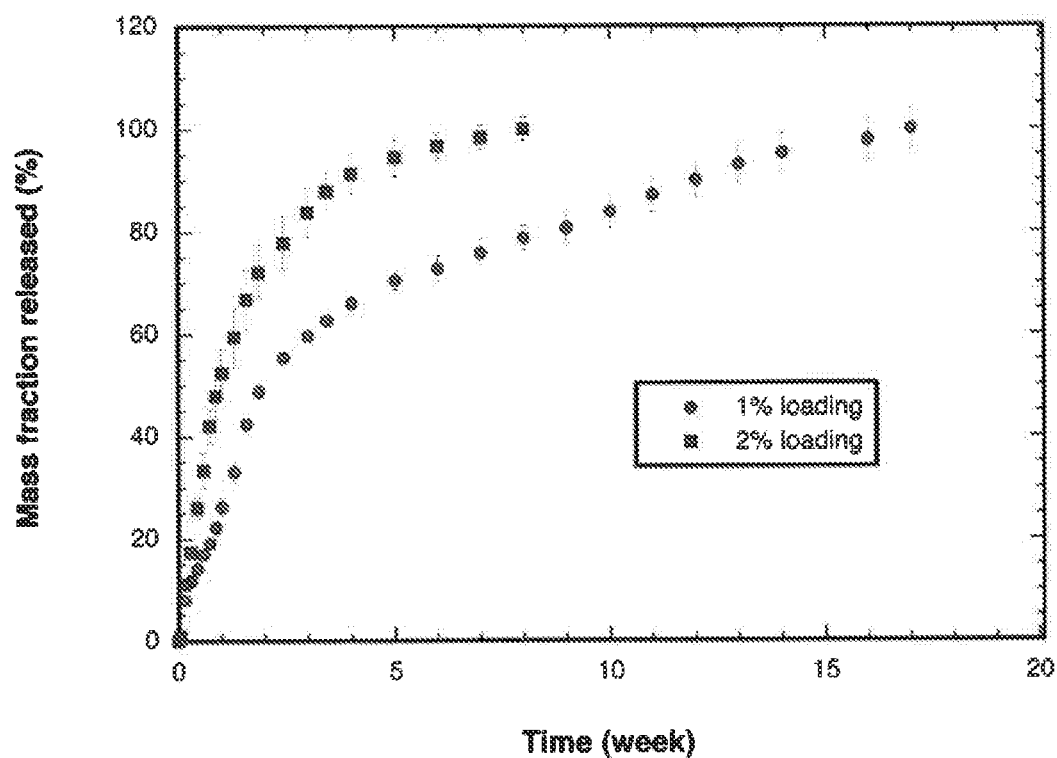
FIG. 15 is a plot showing influence of particle loading on lysozyme release from 1800 Da P(TMC-HTMC) with 30% HTMC.

For each loading condition, release began with a minimal burst release of the initially loaded lysozyme. FIG. 15 shows the influence of particle loading on lysozyme release from 1800 Da P(TMC-HTMC) with 30% HTMC. The burst effect was larger (11% vs. 8%) for the 2% particle loading case vs. the 1% particle loading case, reflecting the increased probability of a particle being exposed at the surface as the number of particles inside the polymer increases. A sustained release was obtained, lasting 8 weeks for the 2% loading case and 17 weeks for the 1% loading case. The release was continuous when the loading was 2%, while a two phase release profile was obtained for 1% loading; an initially faster release period followed by a longer and slower release period which started at approximately 4 weeks. The faster release period is likely a diffusion controlled release phase, while the second slower release period is likely a polymer degradation controlled release phase. Importantly, complete protein release was obtained, indicating that protein aggregation and/or denaturation within the copolymer was minimal.

Figure 16:
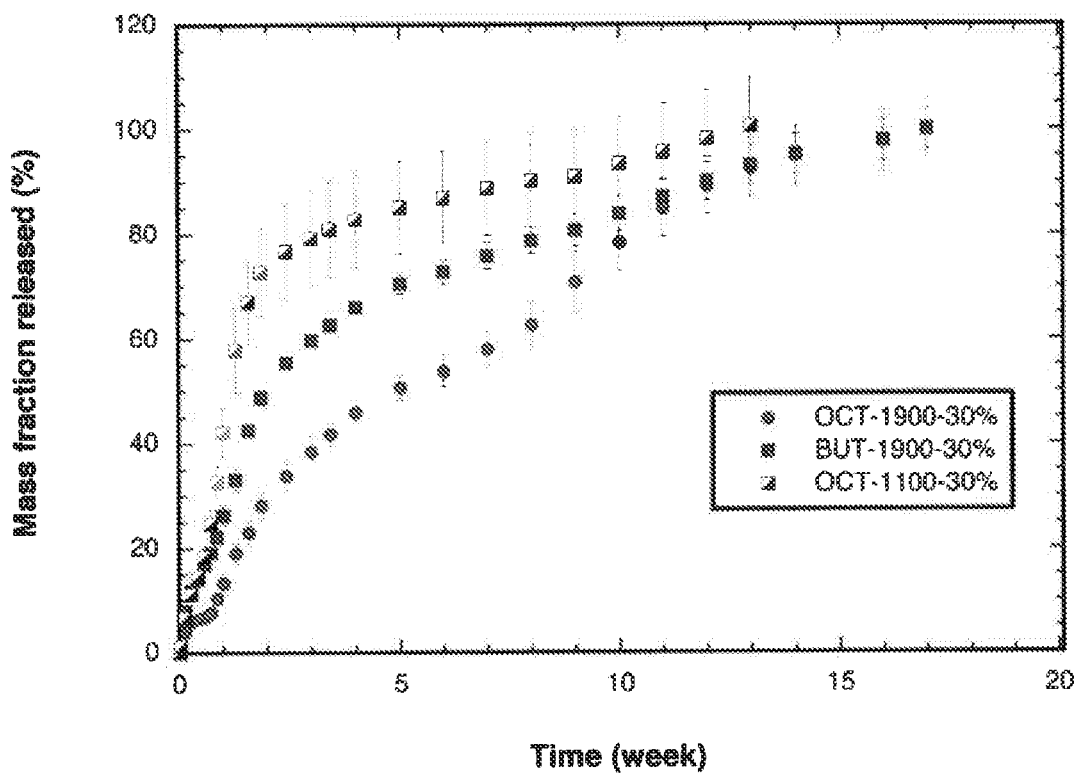
FIG. 16 is a plot showing influence of P(TMC-HTMC) initiator and molecular weight on lysozyme release, wherein the particle loading for each case was 1% (w/w).

The influence of copolymer molecular weight and the hydrophobicity of the initiator used to prepare the copolymer on lysozyme release using a 1% (w/w) particle loading is given in FIG. 16. Again, for each case, release began with a minimal burst effect of less than 10% of the total amount of lysozyme initially loaded into the copolymers. The release of the lysozyme increased as the molecular weight of the copolymer decreased, for a given initiator, and for a given molecular weight, as the hydrophobicity of the initiator decreased. The increase in release rate with respect to molecular weight of the copolymer is attributed to an increase in the contribution of copolymer degradation on lysozyme release, while the increase in release rate with respect to decreased initiator hydrophobicity is due to a combination of the decrease in copolymer degradation rate as well as a decrease in ultimate water content of the copolymer during lysozyme release. And again, complete protein release was observed.

Example 2

The objectives of this study were to determine the in vivo degradation rate and mechanism, and to assess the tissue response to P(TMC-HTMC) following subcutaneous injection in rats. To achieve these goals, the change in molecular weight and copolymer composition were monitored and evaluated as a function of implantation time. The tissue response to P(TMC-HTMC)s was assessed histologically using Masson's trichrome staining and immunohistochemically by staining for CD68 positive (CD68$^+$) cells and compared to the tissue response to the implantation of a clinically used suture, MONOCRYL, which is considered to be biocompatible with a standard degradation time of 13-17 weeks. [18]

Materials 1,3-trimethylene carbonate (TMC) was obtained from Leapchem, Hangzhou, China. 5-benzyloxy trimethylene carbonate (BTMC) was purchased from Obiter research LLC, USA. 1 M hydrogen chloride solution in diethyl ether (HCl.Et2O), palladium on carbon (Pd/C), palladium hydroxide on carbon (Pd(OH)$_2$/C), 1-octanol, 1-butanol, Celite, sodium citrate, Tween 20, bovine serum albumin (≥98% purity) (BSA) and deuterated dimethyl sulfoxide (DMSO-d¬6) were purchased from Sigma-Aldrich Ltd, Canada. Phosphate buffered saline (PBS) powder, tris hydrochloride (TBS), Permount™ mounting medium, anhydrous potassium carbonate (K2CO3), formaldehyde, tetrahydrofuran (THF), methanol (MeOH) and dichloromethane (DCM) were purchased from Thermo Fisher Scientific, Canada. Hydrogen gas (H2) (99.99% purity) was purchased from Linde Ltd, Canada. Water used was of type 1 purity, obtained from a Millipore Milli-Q Plus ultrapure water filtration system. THF and methanol were dried over activated 3 Å molecular sieves. All other materials were used as received.

Wistar rats were received from Charles River Laboratories, Canada. Tramadol was purchased from Chiron Compounding Pharmacy Inc, Canada. Primary antibody (antirat-CD68 antibody [ED1] ab31630), the secondary antibody (goat anti-mouse IgG H&L (Alexa Fluor® 488 (ab150113) and fluoroshield mounting medium with 4',6-diamidino-2-phenylindole (DAPI) (ab104139) were purchased from Abcam, Canada. Masson's trichrome (25088) was purchased from Polysciences Inc, Canada. MONOCRYL* Plus suture 3-0 was purchased from Ethicon, USA.

Synthesis and Characterization of P(TMC-HTMC)

P(TMC-HTMC) initiated with 1-octanol or 1-butanol at 30 mol % HTMC and molecular weight range of 1000-2000 Da was prepared via the following procedure. Initiator was added to a 1.5 M solution of TMC and BTMC in dry DCM. Following this addition, 1 M HCl.Et2O was added to the glass vial to achieve a final monomer concentration of 1 M and a monomer to catalyst ratio (M/C) of 3:1. To avoid auto-initiation and initiation with water the polymerization reaction was performed under argon at room temperature. The resulting copolymer purified/neutralized by washing in cold MilliQ water three times at 4° C. After each wash, the water pH was checked and adjusted to neutral using $K_2CO_3$.

$^1$H NMR spectra of the resulting copolymers were recorded in DMSO-$d_6$ at room temperature on a 400 MHz Bruker Avance spectrometer. End group fidelity ($\tau$) and $M_n$ were calculated using Equations 1-4.

Thermal properties were determined by a Mettler-Toledo DSC1 differential scanning calorimeter. A heating and cooling rate of 10° C./min was applied for temperature range of −100° C. to 80° C. The $T_g$ was taken as the inflection point of the second heating cycle. Melt viscosity was measured using a Reological Visco Tech controlled stress rheometer at 25° C. and 37° C. A parallel plate stainless steel fixture with a diameter of 20 mm and a 0.5 mm plate gap was used.

In Vivo Biocompatibility and Biodegradation

The following animal study was performed in accordance with the guidelines of the Canadian Council on Animal Care code of ethics governing animal experiment (protocol #Amsden 2015-1627). The study involved subcutaneous injection of the copolymers into the dorsal tissue of male Wistar rats weighing approximately 300 g. Prior to injection, the copolymer vials were decontaminated by exposure to germicidal UV light in a biosafety cabinet (BSC) for 30 min. Then 1 mL sterile syringes were filled with copolymer using an autoclaved metal spatula while in the BSC, and packed in autoclave bags to be transported to the operating room. Prior to injection, the syringes were heated to 37-40° C. to facilitate injection. The rats were anesthetized with 1% isoflurane in oxygen for few minutes to achieve a level of surgical anesthesia as indicated by a lack of tail and corneal reflexes. Once anesthetized, the rats were shaved at the site of implantation, the skin was disinfected using 10% povidone iodine, and washed with saline. To implant the copolymer samples, a small incision was made, and a pocket formed between the skin and the underlying tissue. Then approximately 100 mg of the pre-heated copolymer was injected into the pocket through a 18½ gauge needle, and the pocket was closed using suture wound clips. Two implantation sites for each copolymer composition on the dorsal area of each rat were provided. The mass of injection was determined by weighing the syringe plus needle before and after each injection. A small piece of MONOCRYL™ Plus 3-0 suture of about 1 cm length was implanted as a control in the same manner. After implantation, tramadol was injected subcutaneously at a dose of 20 mg/kg body weight. The tramadol injection was repeated every 24 h for 3 days. The day following implantation, and every 2 to 3 days afterwards, the animals were observed for signs of unusual behavior including avoidance of other animals, lack of grooming, dull or cloudy eyes, diarrhea, increased respiration, aggression, salivation, listlessness, dehydration, and chattering. After 1, 2, 4, 12 and 22 weeks, two rats were chosen randomly and humanely euthanized by the injection of a lethal dose of Euthanyl at 120 mg/kg body weight. The site of implantation was shaved, and the skin was dissected back. A photograph of the surrounding tissue was taken and the tissue was visually assessed for signs of inflammation and necrosis. To determine the in vivo degradation mechanism, from each rat one injection site of each copolymer composition was opened by a surgical scalpel blade and the remaining copolymer was removed from the site using a spatula. The chemical structure of the harvested copolymer was analyzed as described above.

Histological and Immunohistochemistry Analysis

The harvested tissue was fixed in 4 wt % paraformaldehyde in PBS immediately after extraction and stored overnight in a refrigerator at 4° C. Then tissues were transferred to 75 vol % ethanol and stored in a refrigerator at 4° C. until processing. The resulting tissues were dehydrated in graded ethanol (75% and then 100%), cleared in xylene, and then embedded in paraffin. The tissue blocks in paraffin were cut at 10 µm intervals and deparaffinized by immersing in xylene, graded ethanol (100%, 50% and then 25%) and PBS, respectively. Finally, the tissue sections were stained with a Masson's trichrome stain kit according to the supplier's instructions. The stained sections were dehydrated using xylene and ethanol, and cover-slipped with Permount™ mounting medium. All images were obtained using a Zeiss Axiocam microscope camera equipped with Axio Vision software (version 4.7.1.0) using a microscope objective of 20×. A total of 5 images were captured per slide. The thickness of the fibrous capsule and the number of the cells per $10^4$ µm$^2$ distributed in the inflammatory zone at a distance of 100-300 µm from the copolymer-tissue interface was measured from these images using ImageJ software.

For immunohistochemistry (IHC) analyses, the deparaffinized tissue sections were subjected to heat-mediated antigen retrieval in pH 6 citrate buffer bath at 60° C. overnight and then washed in a bath of 1×TBS-0.025% Tween 20 at room temperature. The endogenous peroxide activity was blocked using 5000 µg/mL BSA in TBS for 30 min at room temperature. The primary antibody (mouse anti rat-CD68 antibody) diluted in 1% BSA solution in 1×TBS at 1:400 dilution was applied on the sections and incubated at 4° C. in a refrigerator overnight. The day after, the slides were washed by immersion in a bath of 1×TBS-0.025% Tween 20 with gentle agitation. The secondary antibody (goat anti mouse IgG Alexafluor488) diluted in 1×TBS at 1:500 dilution was applied on the sections and incubated at room temperature in a dark room for 1 h. Finally, sections were mounted in Fluoroshield mounting medium with DAPI and cover-slipped in a dark room. Tissue sections of spleen at a thickness of 10 μm were used on a separate slide as a positive control. Slides were stored in a refrigerator at 4° C. in a closed box with no exposure to light. Each IHC slide included one negative control. For the negative control, the primary antibody was replaced by 1% BSA solution in 1×TBS. This protocol was optimized based on the immunohistochemistry application guide and instructions from Abcam. All images were taken with a Zeiss Axio Imager M1 microscope camera equipped with ZEN blue software using a microscope objective of 40×. A total of 8 images were captured per slide and the number of CD68+ cells per 104 μm2 distributed in the inflammatory zone at a distance of 100-300 μm from the copolymer-tissue interface was measured using ZEN blue software.

Statistical Analysis

The chemical composition and number average molecular weight of the extracted copolymers were measured on duplicate samples. All data are reported as the average±the standard deviation about the average. Statistical differences were determined using a one-way ANOVA. Differences were considered significant for p values less than 0.05.

The thickness of the fibrous capsule and the density of the cells for each copolymer composition were averaged for implantation sites from 5 images for histological analysis (N=5) and 8 images for immunohistochemically analysis (N=8) on two different rats (n=2) at each time point. Statistical differences were determined using a two-way ANOVA with a Bonferroni post-hoc test. Differences were considered significant for p values less than 0.05.

Results and Discussion

Copolymer Properties.

A series of 1000-2000 Da copolymers initiated with 1-butanol or 1-octanol and having a 30 mol % HTMC content were prepared using HCl.Et2O. Table 5 shows the physical-chemical properties of the resulting purified copolymers.

TABLE 5

Physical-chemical properties of P(TMC-HTMC) copolymers

| Sample | Initiator | Mn (Da) | Tg (° C.) | HTMC (%) | Viscosity at 37° C. (Pa · s) |
|---|---|---|---|---|---|
| OCT-P10-30H | 1-octanol | 1160 | −35 | 30 | 15 ± 1.8 |
| OCT-P18-30H | 1-octanol | 1740 | −26 | 28 | 92 ± 2.3 |
| BU-P18-30H | 1-butanol | 1730 | −25 | 29 | 98 ± 4.7 |

Visual Observation and In Vivo Biodegradation.

The copolymer pre-heated to 40° C. was injected easily through an 18½ gauge needle and into the tissue pocket formed in the subcutaneous space. During the period of the study all the animals gained weight and no signs of discomfort or adverse response such as sores and redness were observed around the injection sites. A photograph of the surrounding tissue was taken after euthanization and exposure of the injection site, and the tissue around the injection site was visually assessed. The injected copolymers formed a depot at the implantation site which was readily observed at each time point.

Figure 17A:
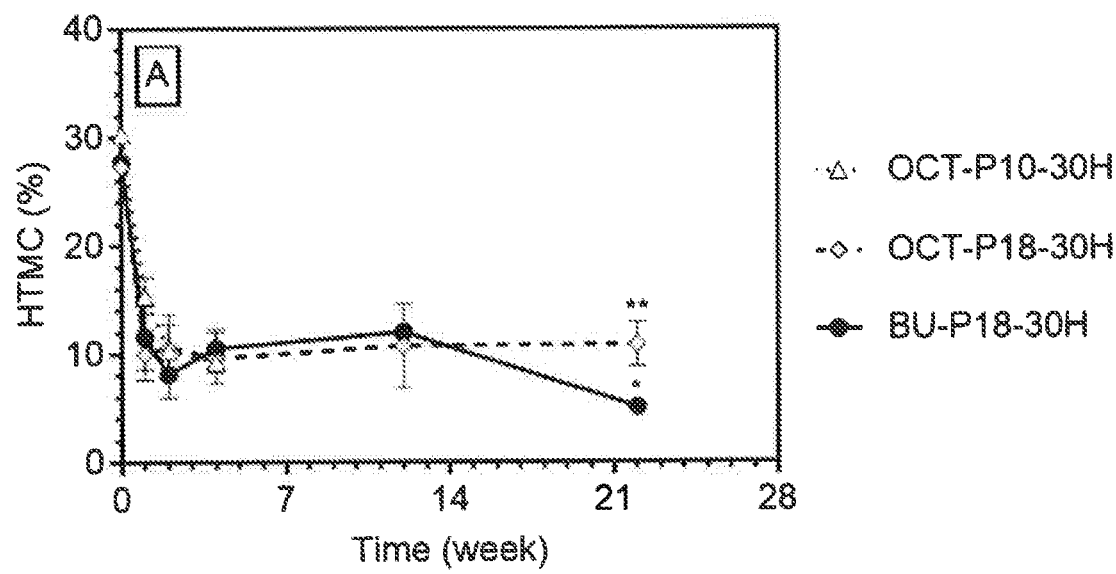
FIGS. 17A and 17B are plots showing evolution of HTMC mole % and $M_n$ (Da), respectively, during in vivo degradation, wherein each data point represents the average and the error bars are the standard deviation about the average; statistical difference between week 22 with previous time points (*), statistical difference between OCT-P18-30H with B-P18-30H at the same time point (**), $p<0.05$, one-way ANOVA, n=2.
Figure 17B:
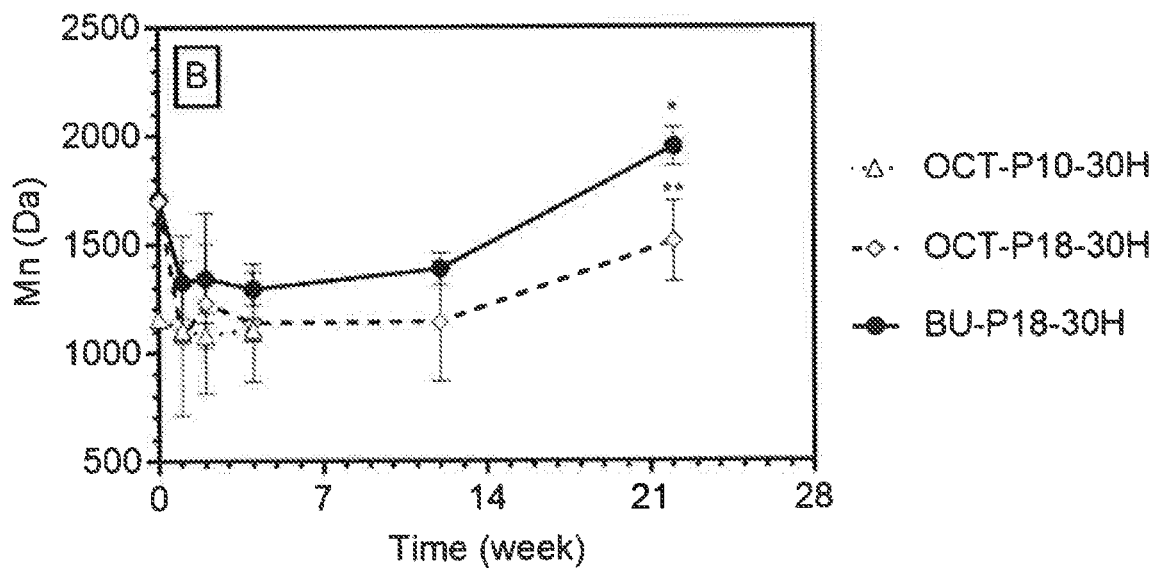

FIGS. 17A and 17B show the change HTMC mol % and in the number average molecular weight ($M_n$), respectively, of the remaining copolymer over the 22 weeks of the in vivo study. By week 1, the remaining copolymer samples had lost 55-60% of their initial HTMC content. The HTMC composition of the copolymers then stayed fairly constant with time at approximately 10 mol % except for BU-P18-30H, which showed a significant decrease in HTMC composition to 5±0.6 mol % by week 22 (p value<0.05). For the copolymer compositions with an initial $M_n$ of approximately 1700 Da, a 20-40% decrease in $M_n$ was observed over the first week. The $M_n$ then stayed constant up to week 12. By week 22, the $M_n$ had not changed significantly for OCT-P18-30H samples; however, a significant increase was observed in the $M_n$ of the BU-P18-30H samples (p value<0.05). In contrast, the $M_n$ remained constant for OCT-P10-30H until week 4, after which the polymer depot had disappeared.

Figure 18A:
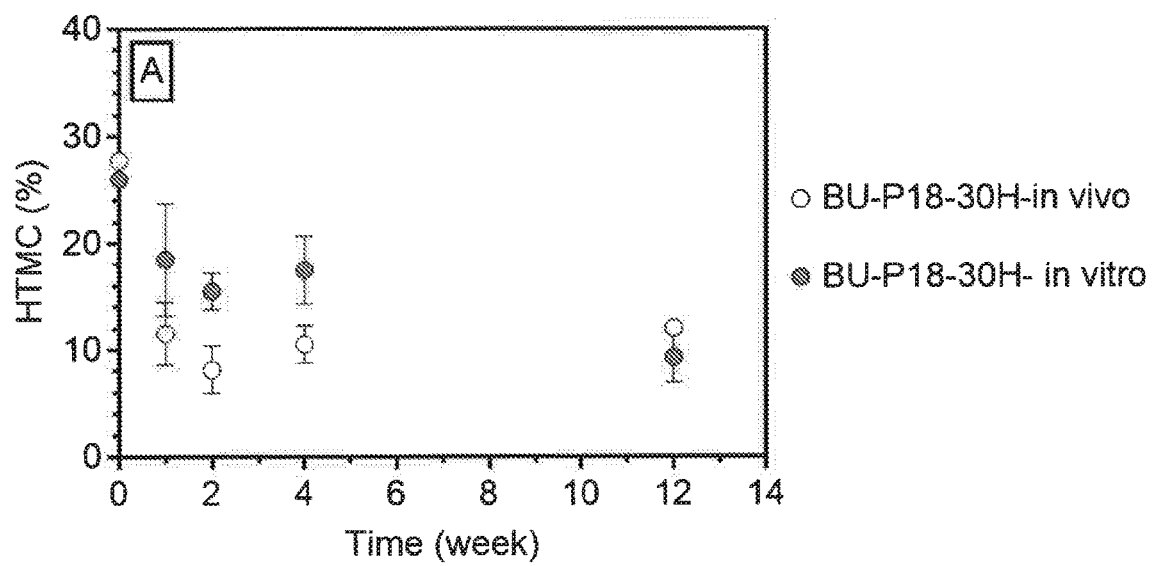
FIGS. 18A and 18B are plots showing in vive versus in vitro degradation changes in HTMC mole % and $M_n$ (Da), respectively, of BU-P18-30H samples, wherein each data point represents the average and the error bars are the standard deviation about the average.
Figure 18B:
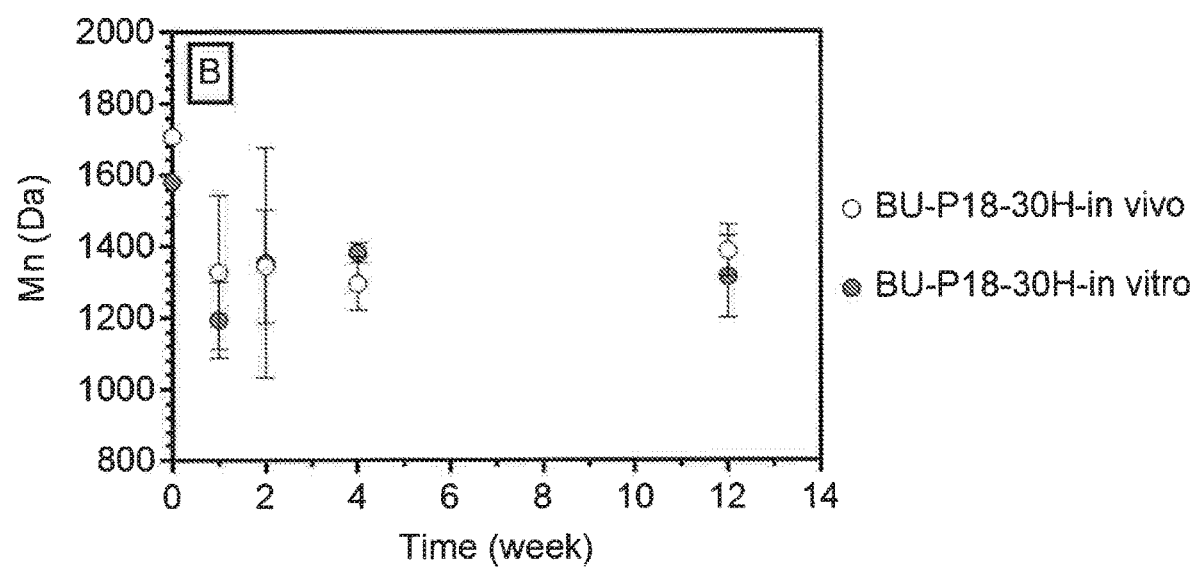

According to these results, HTMC units along the backbone were rapidly lost from the copolymer within a week in the body, resulting in the production of lower molecular weight chains containing principally TMC. A statistical comparison using two-way ANOVA of these in vive results with previous in vitro degradation (PBS, 37° C.) results revealed no significant difference in the $M_n$ and HTMC content of the remaining copolymers under in vitro and in vivo conditions at the same time points up to week 12. FIGS. 18A and 18B show representative comparisons of the change in HTMC content and $M_n$ for BU-P18-30H samples under in vive and in vitro conditions. OCT-P18-30H and OCT-P10-30H samples exhibited similar results.

Histological and Immunohistochemistry Analysis.

Harvested tissue sections were stained with Masson's trichrome to determine the host tissue response to the copolymers. Masson's trichrome stains collagen blue, cytoplasm and muscle fiber red, and nuclei black. Stained tissue sections obtained at different time points were chosen randomly and examined. All the injected copolymers initially formed cohesive depots, but with some small copolymer droplets in the tissue surrounding the injection site that were observed up to week 4. Histological images confirmed that by week 12 the suture and OCT-P10-30H had disappeared; however, OCT-P18-30H and BU-P18-30H could still be found in the tissue at week 22.

Figure 19:
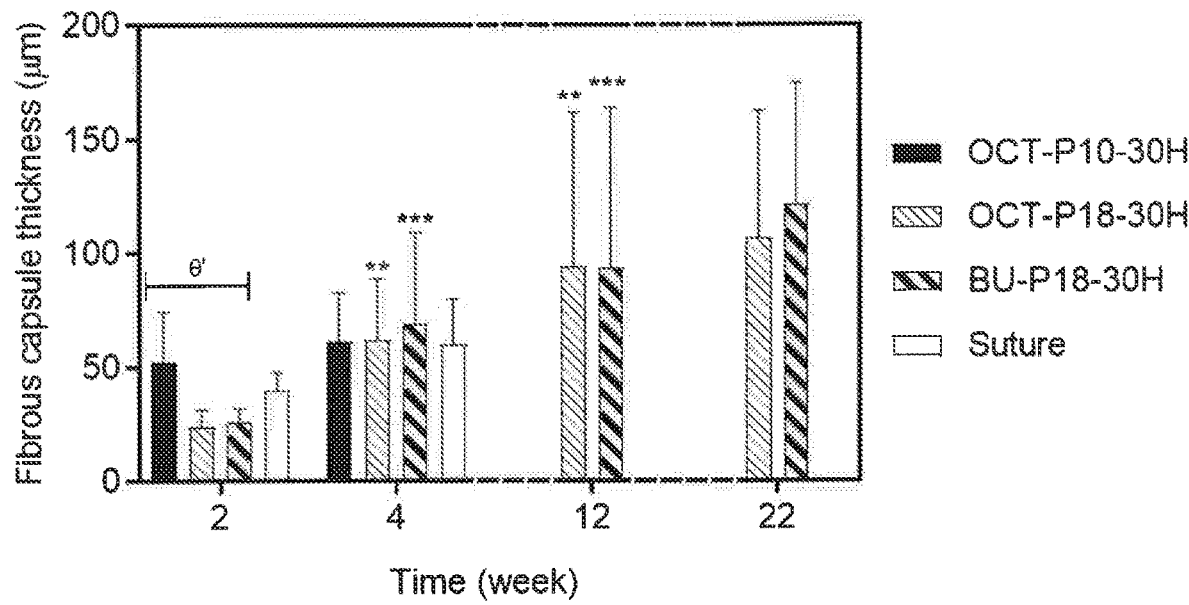
FIG. 19 is a plot showing thickness of the fibrous capsule formed around the implants at 2, 4, 12, and 22 weeks following subcutaneous injection in Wistar rats, wherein error bars indicate the standard deviation of 5 images of each sample (N=5) on two different rats (n=2). Statistical difference with the previous time point for OCT-P18-30H () and BU-P18-30H (*), $p<0.01$. Statistical difference between OCT-P10-30H with other copolymers at the same time point (θ'), $p<0.05$. Two-way ANOVA with Bonferroni post-hoc test.
Figure 20:
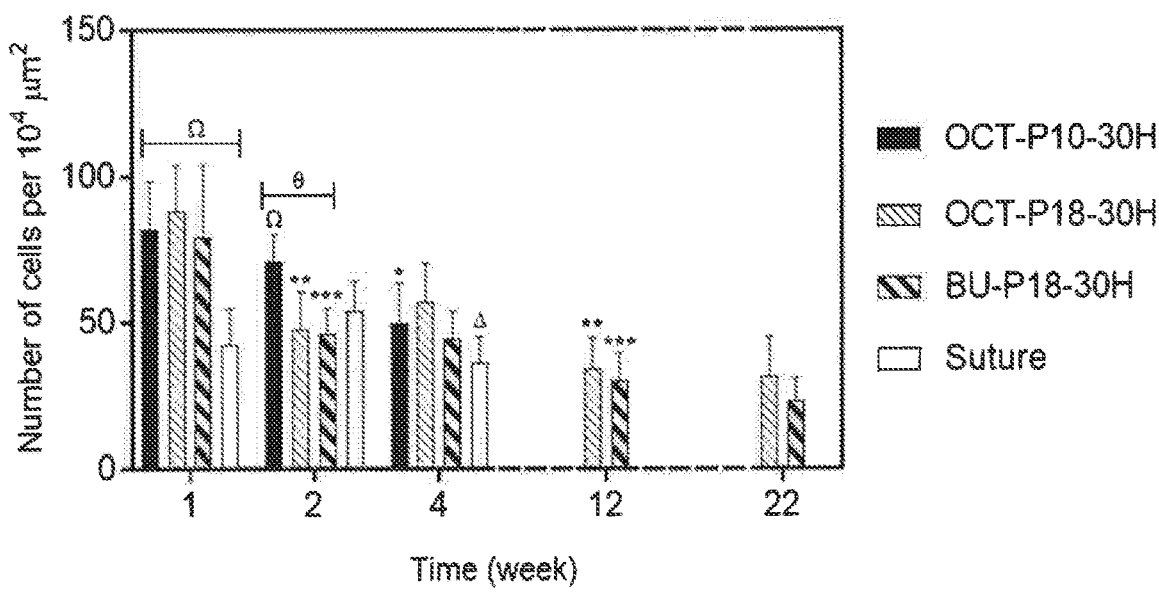
FIG. 20 is a plot showing number of cells at the copolymer-tissue interface and the surrounding fibrous capsule per $10^4$ μm$^2$ after 1 to 22 weeks of subcutaneous injection in Wistar rats, wherein the error bars indicate the standard deviation of 5 images of each sample (N=5) on two different rats (n=2). Statistical difference with the previous time point for OCT-P10-30H (*), OCT-P18-30H (), BU-P18-30H (*) and suture (Δ), statistical difference between OCT-P10-30H with other copolymers at the same time point (θ), statistical difference between suture with copolymers at the same time point (Ω), $p<0.01$, Two-way ANOVA with Bonferroni post-hoc test.

The thickness of the fibrous capsule and the number of the cells present in the inflammatory zone 0-300 μm from the copolymer-tissue interface were measured using ImageJ software (FIGS. 19 and 20, respectively). The number of cells per area and the thickness of the fibrous capsule around the copolymer droplets were also analyzed. By week 2 a fibrous capsule layer had formed around the injected copolymers and the suture with a range of average thickness of 24-53 μm. The capsule surrounding the OCT-P10-30H samples was significantly thicker than that around the other copolymers. The thickness of the fibrous capsule did not change significantly at week 4 for both the suture and the OCT-P10-30H. The higher molecular weight copolymer samples, OCT-P18-30H and BU-P18-30H, showed a significant gradual increase in the thickness of the fibrous capsule over time from week 2 to 12 which stabilized by week 22. There was no significant difference in capsule thickness between the copolymers themselves and between the suture and the copolymers from week 4 to 22.

As shown in FIG. 20, there were several layers of infiltrated cells at week 1, likely fibroblasts, neutrophils, and macrophages, with no evidence of fibrous capsule formation. Cells distributed at the inflammatory zone with the range of average thickness of 175-200 μm which was significantly thicker than the inflammatory zone around the tissue-suture interface with the thickness of 70±33 μm. All three copolymers had a significantly greater density of cells (range of average cell density=80-88 cells/$10^4$ $\mu m^2$) present at the tissue-copolymer interface than was present at the tissue-suture interface (average cell density=42±12 cells/$10^4$ $\mu m^2$). There was no significant difference in cell density at the tissue-copolymer interface between the copolymers at week 1. By week 2, the thickness of the inflammatory zone surrounding the tissue-copolymer interface decreased significantly to 86-100 $\mu m$, which was similar in range to that around the suture. By week 2 and 4, the number of cells at the tissue-copolymer interface and within the surrounding inflammatory zone significantly decreased compared to the previous weeks. Also, no significant difference in the cell density in the inflammatory zone was observed between copolymers themselves and between the copolymers and the suture at week 4 (range of average cell density (46-57 cells/$10^4$ $\mu m^2$)). By week 12, the cell density in the inflammatory zone around the copolymers that remained, OCT-P18-30H and BU-P18-30H, decreased significantly in comparison to week 4. The cell density in the inflammatory zone around these copolymers had stabilized by week 22. No significant difference was observed in the cell density in the inflammatory zone between the copolymers themselves or between the copolymers and the suture from week 4 to week 22.

Figure 21:
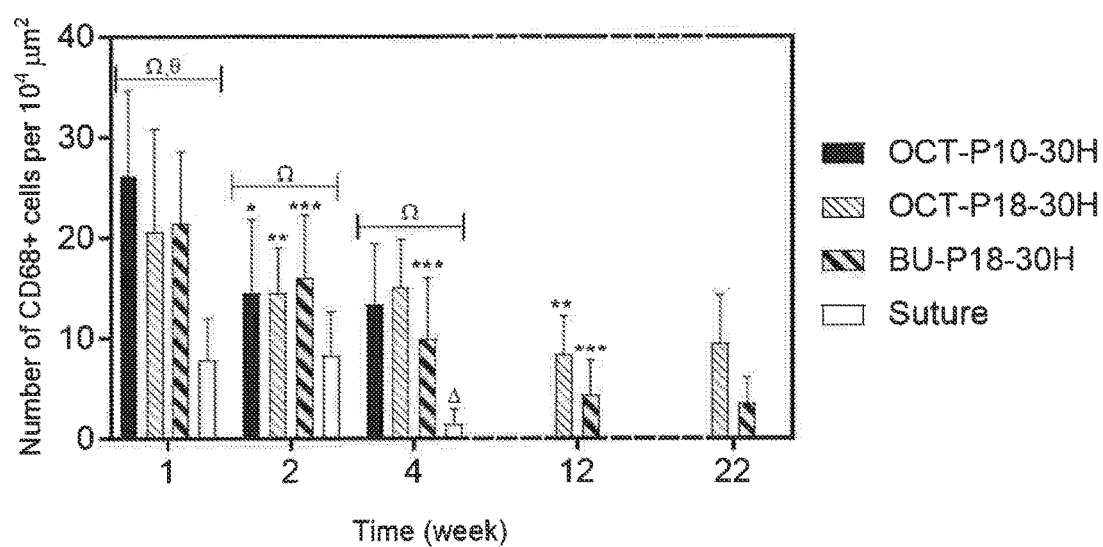
FIG. 21 is a plot showing number of CD68+ cells at the copolymer-tissue interface and the surrounding fibrous capsule per $10^4$ μm$^2$ after 1 to 22 weeks of subcutaneous injection in Wistar rats, wherein error bars indicate the standard deviation of 8 images of each sample (N=8) on two different rats (n=2). Statistical difference with the previous time point for OCT-P10-30H (*), OCT-P18-30H (), BU-P18-30H (*) and suture (Δ), statistical difference between OCT-P10-30H with other copolymers at the same time point (θ), statistical difference between suture with copolymers at the same time point (Ω), p<0.01, two-way ANOVA with Bonferroni post-hoc test.

The continued presence of macrophages at the tissue-copolymer interface is a sign of chronic inflammation. To quantify the number of macrophages at the tissue-copolymer interface, the tissue sections were immunostained with the pan-macrophage marker CD68. Tissue sections were chosen randomly, and images for CD68+ staining in tissue surrounding BU-P18-30H samples as well as the suture control were analyzed for different time points. From the analysis of the Masson's trichrome images of the inflammatory zone thickness, the region of interest was taken as 0-300 $\mu m$ from the copolymer/suture-tissue interface. The number of monocytes/macrophages ($CD68^+$ cells) within this selected area was counted and reported as the number of $CD68^+$ cells/$10^4$ $\mu m^2$ (FIG. 21). CD68+ cells around the copolymer droplets in the tissue within the same region of interest were also counted.

By week 1, there was a significantly greater density of $CD68^+$ cells present within the inflammatory zone around the implanted copolymers than within the inflammatory zone around the suture. Also, a significantly higher CD68+ cell density was observed around the OCT-P10-30H copolymer than in the inflammatory zone around the other copolymers. By weeks 2 and 4, the $CD68^+$ cell density at the tissue-copolymer and tissue-suture interfaces as well as within the surrounding inflammatory zone significantly decreased compared to the previous weeks.

Furthermore, the $CD68^+$ cell density was significantly higher around the copolymers than in the inflammatory zone around the suture. By week 12, the $CD68^+$ cell density decreased significantly for the remaining copolymers OCT-P18-30H and BU-P18-30H in comparison to week 4 which stabilized fairly by week 22. No significant difference was observed between the copolymers from week 2 to week 22.

All the P(TMC-HTMC) copolymers exhibited almost the same tissue response. A slightly higher total cell density, higher CD68+ cell density, and a thicker fibrous capsule was observed around the lower molecular weight OCT-P10-30H in week 1 and 2. This result may be due to its faster degradation and subsequent release of a greater amount of degradation products with time in comparison to the other copolymers. The faster degradation resulted in a more intense but briefer inflammatory response to the implantation of the OCT-P10-30H as compared to the OCT-P18-30H and BU-P18-30H. At the later time point of 12 weeks, the Monocryl suture and OCT-P10-30H completely disappeared while OCT-P18-30H and BU-P18-30H samples still remained in the tissue. Moreover, these samples were surrounded by fewer macrophages and a thicker fibrous capsule at this time in comparison to week 4. The inflammatory response stabilized by week 22 around these copolymers.

The tissue surrounding the P(TMC-HTMC) copolymers exhibited a higher total cell density at week 1 than was found for the suture; however, no significant difference was observed in the later time points. Also, a significantly higher CD68+ cell density was observed in the tissue surrounding all the copolymers than around the suture at different time points. The higher total cell density at week 1 and higher CD68+ cell density over time around the copolymers than around the suture may be due to differences in the implantation method. The suture was placed with forceps into the pocket formed between the skin and the underlying tissue. In contrast, the copolymer samples were injected into the pocket through a syringe. While injecting the copolymer, the movement of the needle within the pocket formed in the tissue and its contact with tissue may have caused greater trauma and subsequently a more severe acute inflammatory response. In addition to the difference in the implantation method, other parameters that can influence the tissue response include the surface chemistry, mechanical strength and the degradation products of the implant. MONOCRYL suture is a solid filament composed of 25% $\epsilon$-caprolactone and 75% glycolic acid repeating units, [18] while the P(HTMC-TMC) copolymer is a viscous liquid and is composed of TMC and HTMC repeating units. Degradation of the suture leads to the release of glycolic acid as well as short oligomers mainly composed of $\epsilon$-caprolactone, which are different than the glycerol, $CO_2$, and the short oligomers mainly composed of TMC resulting from the degradation of P(TMC-HTMC).

CONCLUSION

This study of the in vivo degradation and the tissue response of the injectable P(TMC-HTMC) revealed quick degradation of the HTMC units followed by gradual elimination of the short chains produced via HTMC cleavage. The lower molecular weight copolymer OCT-P10-30H exhibited a more rapid degradation rate due to the fewer backbone cleavage events required to produce water-soluble short chains. P(TMC-HTMC)s within the molecular range of 1000-2000 Da and 30 mol % HTMC content initiated with either 1-octanol or 1-butanol exhibited the same inflammatory response, which subsided in the later weeks of the study. The observed tissue response was comparable to the tissue response of the commercial and clinically used MONOCRYL suture, suggesting that these new materials can be considered equivalently biocompatible.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

[1] A. Hatefi, B. Amsden, Biodegradable injectable in situ forming drug delivery systems, J Controlled Release. 80 (2002) 9-28.

[2] B. G. Amsden, Liquid, injectable, hydrophobic and biodegradable polymers as drug delivery vehicles, Macromol. Biosci. 10 (2010) 825-835. doi:10.1002/mabi.200900465.

[3] M. van de Weert, R. van Dijkhuizen-Radersma, J. Bezemer, W. Hennink, D. Crommelin, Reversible aggregation of lysozyme in a biodegradable amphiphilic multiblock copolymer, Eur J Pharm Biopharm. 54 (2002) 89-93.

[4] K. Schwach-Abdellaoui, P. Loup, N. Vivien-Castioni, A. Mombelli, P. Baehni, J. Barr, et al., Bioerodible injectable poly(ortho ester) for tetracycline controlled delivery to periodontal pockets: Preliminary trial in humans, Aaps Pharmsci. 4 (2002) 20.

[5] K. Schwach-Abdellaoui, R. Gurny, J. Heller, J. Barr, Control of Molecular Weight for Auto-Catalyzed Poly(ortho ester) Obtained by Polycondensation Reaction, International Journal of Polymer Analysis and Characterization. 7 (2002) 145-161. doi:10.1080/10236660214593.

[6] A. Hatefi, D. Knight, B. Amsden, A biodegradable injectable thermoplastic for localized camptothecin delivery, J. Pharm. Sci. 93 (2004) 1195-1204. doi:10.1002/jps.20045.

[7] M. Sokolsky-Papkov, L. Golovanevski, A. J. Domb, C. F. Weiniger, Prolonged local anesthetic action through slow release from poly (lactic acid co castor oil), Pharm Res. 26 (2009) 32-39. doi:10.1007/s11095-008-9699-8.

[8] R. Bezwada, Liquid Copolymers of Epsilon-Caprolactone and Lactide, U.S. Pat. No. 5,442,033, 1995.

[9] R. Bezwada, S. Arnold, Liquid absorbable copolymers for parenteral applications, U.S. Pat. No. 5,631,015, 1997.

[10] T. Trimaille, R. Gurny, M. Moller, Poly(hexyl-substituted lactides): Novel injectable hydrophobic drug delivery systems, J. Biomed. Mater. Res., Part A. 80A (2007) 55-65.

[11] L. Timbart, M. Y. Tse, S. C. Pang, O. Babasola, B. G. Amsden, Low viscosity poly(trimethylene carbonate) for localized drug delivery: rheological properties and in vivo degradation, Macromol. Biosci. 9 (2009) 786-794. doi:10.1002/mabi.200800318.

[12] A. Nathan, M. C. Melican, K. R. Brown, M. C. Zimmerman, Bone replacement materials utilizing bioabsorbable liquid polymers, U.S. Pat. No. 7,005,136, 2006.

[13] O. I. Babasola, B. G. Amsden, Surface eroding, liquid injectable polymers based on 5-ethylene ketal ε-caprolactone, Biomacromolecules. 12 (2011) 3423-3431. doi:10.1021/bm200980a.

[14] I. O. Babasola, W. Zhang, B. G. Amsden, Osmotic pressure driven protein release from viscous liquid, hydrophobic polymers based on 5-ethylene ketal ε-caprolactone: potential and mechanism, Eur J Pharm Biopharm. 85 (2013) 765-772. doi:10.1016/j.ejpb.2013.04.009.

[15] J. P. Jain, S. Modi, N. Kumar, Hydroxy fatty acid based polyanhydride as drug delivery system: Synthesis, characterization, in vitro degradation, drug release, and biocompatibility, J. Biomed. Mater. Res., Part A. 84A (2008) 740-752.

[16] B. Amsden, A. Hatefi, D. Knight, E. Bravo-Grimaldo, Development of biodegradable injectable thermoplastic oligomers, Biomacromolecules. 5 (2004) 637-642. doi:10.1021/bm034457n.

[17] F. Q. Yu, R. X. Zhuo, Synthesis and characterization of OH-terminated poly(trimethylene carbonate)s by alcohol-initiated ring-opening polymerization in melt bulk without using any catalyst, Polymer Journal. 36 (2004) 28-33. doi:10.1295/polymj.36.28.

[18] G. Molea, et al., Comparative study on biocompatibility and absorption times of three absorbable monofilament suture materials (Polydioxanone, Poliglecaprone 25, Glycomer 631), Br J Plast Surg. 53 (2000) 137-141. doi:10.1054/bjps.1999.3247.

The invention claimed is:

1. An injectable, biodegradable, biocompatible liquid copolymer, comprising:
   trimethylene carbonate (TMC);
   5-hydroxy trimethylene carbonate (HTMC); and
   at least one initiator selected from an alcohol, an amine, and a thiol;
   wherein the initiator is attached to one end of the copolymer along a copolymer backbone and hydrophobicity of the initiator controls a degradation rate of the copolymer;
   wherein a molecular weight (MW) of the copolymer is from about 500 Da to about 5000 Da;
   wherein the copolymer is a liquid with a viscosity of less than about 100 Pa s at a temperature range from 25° C. to 37° C.;
   wherein the copolymer comprises a pendant hydroxyl group on a central carbon of the trimethylene of the HTMC that cleaves the copolymer backbone;
   wherein the degradation rate of the copolymer is a loss of at least 60% of copolymer mass after 56 days in physiologic conditions.

2. The injectable, biodegradable, biocompatible liquid copolymer of claim 1, wherein the degradation rate of the copolymer is also controlled according to a ratio of TMC:HTMC.

3. The injectable, biodegradable, biocompatible liquid copolymer of claim 2, wherein the ratio of TMC:HTMC is from 15:1 to 1:9.

4. The injectable, biodegradable, biocompatible liquid copolymer of claim 1, wherein the amount of the initiator is selected to be from about 1% w/w to about 50% w/w of the MW of the copolymer.

5. The injectable, biodegradable, biocompatible liquid copolymer of claim 1, wherein the initiator is an alcohol.

6. The injectable, biodegradable, biocompatible liquid copolymer of claim 1, wherein the copolymer is biodegradable in vivo;
   wherein degradation yields products that are non-irritating and/or non-toxic and do not cause a substantive change in tissue pH in vivo.

7. The injectable, biodegradable, biocompatible liquid copolymer of claim 1, further comprising at least one drug.

8. The injectable, biodegradable, biocompatible liquid copolymer of claim 7, wherein the drug comprises a therapeutic compound, pharmaceutical, biopharmaceutical, bioactive agent, medicament, antineoplastic, hormone, peptide, protein, nucleic acid, vector, virus, antigen, antibody, or combination thereof.

9. The injectable, biodegradable, biocompatible liquid copolymer of claim 1, for use as a drug delivery vehicle.

10. The injectable, biodegradable, biocompatible liquid copolymer of claim 9, wherein the drug comprises a therapeutic compound, pharmaceutical, biopharmaceutical, bioactive agent, medicament, antineoplastic, hormone, peptide, protein, nucleic acid, vector, virus, antigen, antibody, or combination thereof.

11. The injectable, biodegradable, biocompatible liquid copolymer of claim 1, for use as a coating on a surgical device or instrument; or
   for use as a coating on a surgical device or instrument for drug release.

12. A cohesive drug delivery depot, comprising:
the injectable, biodegradable, biocompatible liquid copolymer of claim 1; and
at least one drug.

13. The cohesive drug delivery depot of claim 12, wherein the drug comprises a therapeutic compound, pharmaceutical, biopharmaceutical, bioactive agent, medicament, antineoplastic, hormone, peptide, protein, nucleic acid, vector, virus, antigen, antibody, or combination thereof.

14. A method for preparing an injectable, biodegradable, liquid copolymer, comprising:
combining trimethylene carbonate (TMC) and 5-hydroxy trimethylene carbonate (HTMC) together with at least one initiator selected from an alcohol, an amine, and a thiol;
wherein the initiator is attached to one end of the copolymer along a copolymer backbone and hydrophobicity of the initiator controls a degradation rate of the copolymer;
wherein a molecular weight (MW) of the copolymer is from about 500 Da to about 5000 Da;
wherein the copolymer is a liquid with a viscosity of less than about 100 Pa s at a temperature range from 25° C. to 37° C.;
wherein the copolymer comprises a pendant hydroxyl group on a central carbon of the trimethylene of the HTMC that cleaves the copolymer backbone;
wherein the copolymer remains as a viscous liquid depot, and gradually degrades according to the controlled degradation rate;
wherein the controlled degradation rate is a loss of at least 60% of copolymer mass after 56 days in physiologic conditions.

15. The method of claim 14, comprising selecting an amount of the initiator to be from about 1% w/w to about 50% w/w of the MW of the copolymer;
wherein a viscosity of the copolymer is related to the amount of the initiator.

16. The method of claim 14, comprising selecting a ratio of TMC:HTMC to control a degradation rate of the copolymer.

17. The method of claim 14, further comprising combining at least one drug with the copolymer.

18. The method of claim 17, comprising combining at least one drug selected from a therapeutic compound, pharmaceutical, biopharmaceutical, bioactive agent, medicament, antineoplastic, hormone, peptide, protein, nucleic acid, vector, virus, antigen, antibody, or combination thereof.

19. A method for delivering at least one drug, comprising:
combining the at least one drug with the injectable, biodegradable, liquid copolymer comprising trimethylene carbonate (TMC), 5-hydroxy trimethylene carbonate (HTMC), and an initiator according to claim 1, such that a cohesive drug delivery depot is prepared; and
administering the cohesive drug delivery depot to a subject.

20. The method of claim 19, wherein the drug comprises a therapeutic compound, pharmaceutical, biopharmaceutical, bioactive agent, medicament, antineoplastic, hormone, peptide, protein, nucleic acid, vector, virus, antigen, antibody, or combination thereof.

21. The method of claim 19, wherein the cohesive drug delivery depot is administered by a route selected from parenteral, topical, and transdermal.

22. The injectable, biodegradable, biocompatible liquid copolymer of claim 1, wherein the initiator is an amine.

23. The injectable, biodegradable, biocompatible liquid copolymer of claim 1, wherein the initiator is a thiol.

24. The method of claim 14, wherein the initiator is an alcohol.

25. The method of claim 14, wherein the initiator is an amine.

26. The method of claim 14, wherein the initiator is a thiol.

27. The method of claim 19, wherein the initiator is an alcohol.

28. The method of claim 19, wherein the initiator is an amine.

29. The method of claim 19, wherein the initiator is a thiol.

* * * * *